United States Patent
Straub et al.

(10) Patent No.: US 10,568,886 B2
(45) Date of Patent: Feb. 25, 2020

(54) TARGETING CYB5R3

(71) Applicant: University of Pittsburgh—Of the Commonwealth System of Higher Education, Pittsburgh, PA (US)

(72) Inventors: Adam C. Straub, Pittsburgh, PA (US); Carlos J. Camacho, Pittsburgh, PA (US); Mizanur Rahaman, Pittsburgh, PA (US); Fabio Reinders, Gramsbergen (NL)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 26 days.

(21) Appl. No.: 15/510,636

(22) PCT Filed: Sep. 11, 2015

(86) PCT No.: PCT/US2015/049689
§ 371 (c)(1),
(2) Date: Mar. 10, 2017

(87) PCT Pub. No.: WO2016/040803
PCT Pub. Date: Mar. 17, 2016

(65) Prior Publication Data
US 2017/0224686 A1    Aug. 10, 2017

Related U.S. Application Data

(60) Provisional application No. 62/049,997, filed on Sep. 12, 2014.

(51) Int. Cl.
*A61K 31/513* (2006.01)
(52) U.S. Cl.
CPC .................. *A61K 31/513* (2013.01)
(58) Field of Classification Search
None
See application file for complete search history.

(56) References Cited

FOREIGN PATENT DOCUMENTS

| WO | WO 2003/079986 | 10/2003 |
|---|---|---|
| WO | WO 2004/024701 | 3/2004 |
| WO | WO 2005/060956 | 7/2005 |
| WO | WO 2008/097640 | 8/2008 |
| WO | WO 2014/066392 | 5/2014 |

OTHER PUBLICATIONS

Brown, AFT, Anaphylactic shock: mechanisms and treatment, 1995, Journal of Accident and Emergency Medicine, 12, pp. 89-100 (Year: 1995).*
Evgenov, "NO-independent stimulators and activators of soluble guanylate cyclase: discovery and therapeutic potential," *Nature Reviews Drug Discovery*, vol. 5, pp. 755-768, Sep. 2006.
International Search Report and Written Opinion issued for International Application No. PCT/US2015/049689 dated Oct. 22, 2015.
Straub et al., "Endothelial cell expression of hemoglobin α regulates nitric oxide signaling," *Nature*, 491(7424): 473-477, Nov. 15, 2012.

* cited by examiner

*Primary Examiner* — Jeffrey S Lundgren
*Assistant Examiner* — Tori Strong
(74) *Attorney, Agent, or Firm* — Klarquist Sparkman, LLP

(57) ABSTRACT

A method for regulating arterial vascular tone in a subject, comprising administering to a subject in need thereof, a therapeutically effective amount of a compound, or a pharmaceutically acceptable salt thereof, having a structure of:

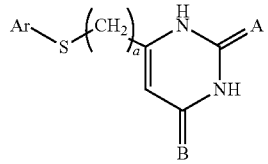

wherein A and B are each individually selected from O or S;
a is 1 to 4; and
Ar is optionally substituted aryl or optionally substituted heteroaryl.

34 Claims, 17 Drawing Sheets screen new molecules

ZINC05626394
IC$_{50}$= 10.84 μM

ZINC39395747
IC$_{50}$= 18.41 μM

ZINC0526268
$IC_{50}$ = 15.08 μM

TARGETING CYB5R3

CROSS REFERENCE TO RELATED APPLICATIONS

This application is the U.S. National Stage of International Application No. PCT/US2015/049689, filed Sep. 11, 2015, which was published in English under PCT Article 21(2), which in turn claims the benefit of U.S. Provisional Application No. 62/049,997, filed Sep. 12, 2014. The provisional application is incorporated herein in its entirety.

ACKNOWLEDGMENT OF GOVERNMENT SUPPORT

This invention was made with government support under grant number HL112904 awarded by the National Institutes of Health. The government has certain rights in the invention.

BACKGROUND

NADH cytochrome b5 reductase 3 (Cyb5R3: NADH: ferricytochrome b5 oxidoreductase, EC1.6.2.2) or methemoglobin reductase is a flavoprotein known for its ability to transfer electrons from the NADH domain of Cyb5R3 to cytochrome b5. Membrane restricted Cyb5R3 in somatic cells regulates several biological reduction reactions including elongation and unsaturation of fatty acids[1], cholesterol biosynthesis and drug metabolism, while the soluble form Cyb5R3 resides in erythrocytes to reduce methemoglobin. In the human population, deficient Cyb5R3 activity leads to recessive hereditary methemoglobinanemia (RHM). Type I RHM displays mildly elevated methemoglobin levels in erythrocytes whereas Type II RHM, which affects all somatic cells, causes severe developmental neurological disorders. Recent evidence suggests that membrane-bound Cyb5R3 expression and activity also contribute to metabolic homeostasis, stress protection and nitric oxide (NO) bioavailability.

Within the vascular wall, the importance of Cyb5R3 in the endothelium has gained appreciation for its role in NO signaling. NO, a naturally produced biogas, contributes to diverse biological processes and is well-known known for its role as a potent vasodilator. Recent evidence revealed α globin expression in small artery and arteriolar endothelial cells where it regulates NO signaling. Enriched in the myoendothelial junctions—the anatomical location where endothelium and vascular smooth muscle make contact—α globin controls NO diffusion to vascular smooth muscle. This process is carried out via biochemical reactions of NO with α globin, whereby synthesized NO from endothelial oxide synthase can react with oxygen bound ferrous heme iron ($Fe^{2+}$) α globin resulting in NO scavenging. However, ferric heme iron ($Fe^{3+}$) α globin permits NO diffusion through a slow and weak reaction. Serving as a switch to control the heme iron redox state of α globin, Cyb5R3 modulates NO bioavailability and thus arterial vascular tone. Therefore, Cyb5R3 serves as an attractive biological target to increase NO bioavailability in order to augment microcirculatory blood flow and decrease blood pressure in the setting of cardiovascular disease.

Currently, there are no potent small molecule inhibitors that block Cyb5R3 activity. Previous studies demonstrated that propylthiouracil (PTU), a drug designed to treat hyperthyroidism, showed inhibition of Cyb5R3 at a concentration of approximately 275 μM. Nonetheless, it is still unclear how PTU exerts its inhibitory effects at a molecular level. By understanding the mechanistic action by which PTU inhibits Cyb5R3, a new class of inhibitors could emerge.

SUMMARY

Disclosed herein is a method for regulating arterial vascular tone in a subject, comprising administering to a subject in need thereof, a therapeutically effective amount of a compound, or a pharmaceutically acceptable salt thereof, having a structure of:

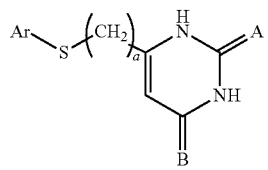

wherein A and B are each individually selected from O or S;

a is 1 to 4; and

Ar is optionally substituted aryl or optionally substituted heteroaryl.

Also disclosed herein is a method for inhibiting cytochrome b5 reductase 3 (Cyb5R3) activity in a subject, comprising administering to a subject in need thereof, an inhibitory amount of a compound, or a pharmaceutically acceptable salt thereof, having a structure of:

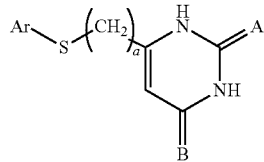

wherein A and B are each individually selected from O or S;

a is 1 to 4; and

Ar is optionally substituted aryl or optionally substituted heteroaryl.

Further disclosed herein is a method for treating massive hemoptysis, GI bleed, epistaxis, migraine headache (post-prodome), musculoskeletal injuries in the acute phase, trauma, hemangioma repair and other intraoperative causes of excessive bleeding, bleeding diatheses, uterine hemorrhage or menorrhagia, septic shock, anaphylactic shock, agioedema, urticaria, or allergic rhinosinusitis in a subject, comprising administering to a subject in need thereof, a therapeutically effective amount of a compound, or a pharmaceutically acceptable salt thereof, having a structure of:

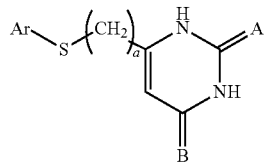

wherein A and B are each individually selected from O or S;

a is 1 to 4; and

Ar is optionally substituted aryl or optionally substituted heteroaryl.

Additionally disclosed herein is a method for treating claudication, erectile dysfunction, myocardial infarction, musculoskeletal/sport injuries in the repair phase, Raynaud's, hypertension, diabetic vasculopathy, or cardiogenic shock in a subject, comprising administering to a subject in need thereof, a therapeutically effective amount of a compound, or a pharmaceutically acceptable salt thereof, having a structure of:

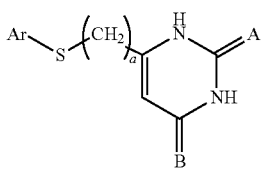

wherein A and B are each individually selected from O or S;

a is 1 to 4; and

Ar is optionally substituted aryl or optionally substituted heteroaryl.

Also disclosed herein is a method for regulating sGC expression, nitric oxide signal transduction and cGMP levels in primary vascular smooth muscle, comprising contacting vascular smooth muscle with a compound, or a pharmaceutically acceptable salt thereof, having a structure of:

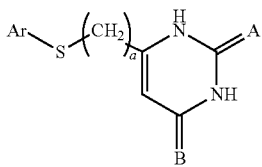

wherein A and B are each individually selected from O or S;

a is 1 to 4; and

Ar is optionally substituted aryl or optionally substituted heteroaryl.

The foregoing will become more apparent from the following detailed description, which proceeds with reference to the accompanying figures.

DETAILED DESCRIPTION

Terminology

Figure 1:
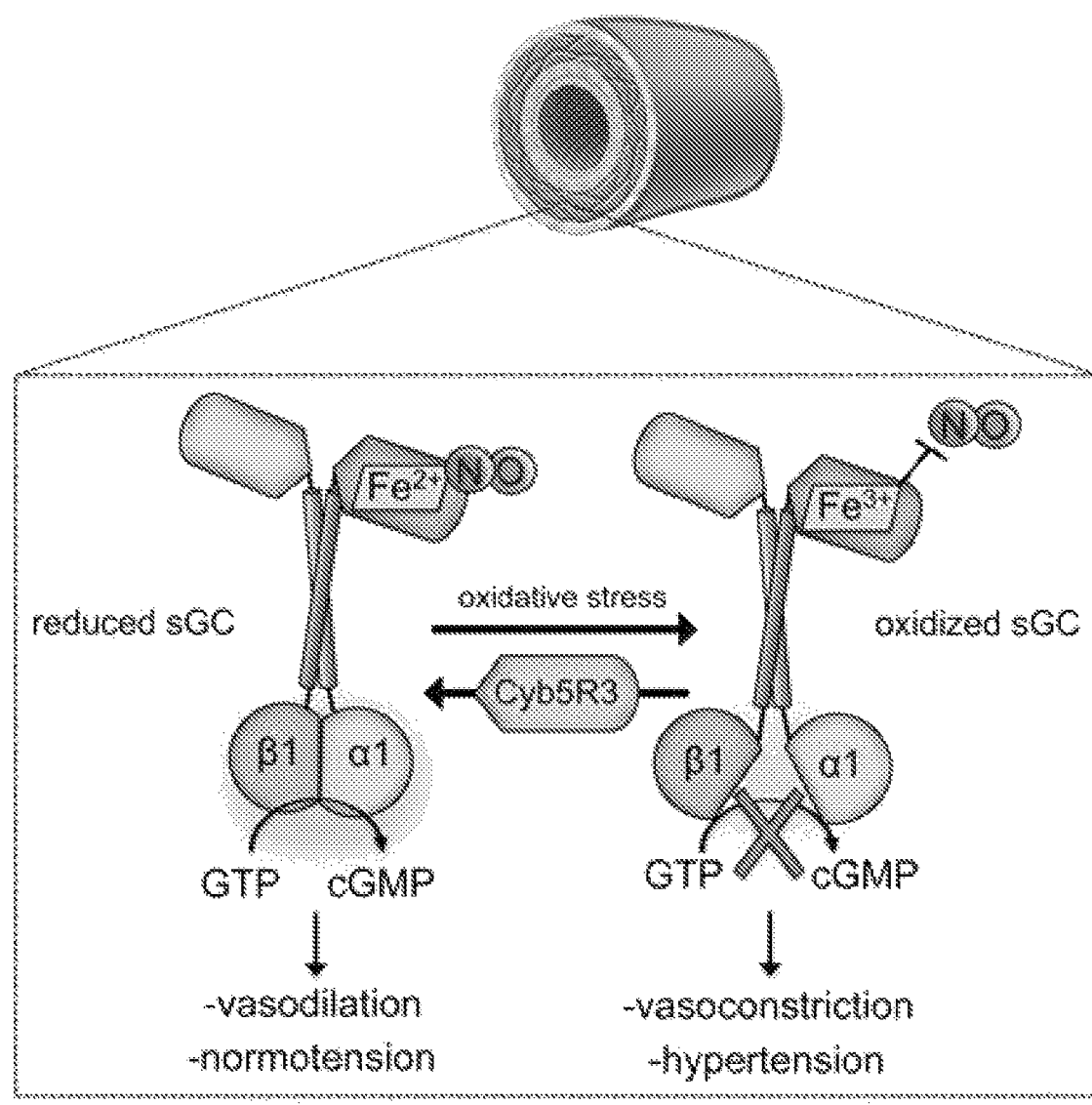
FIG. 1. Overview showing that CyB5R3 sensitizes soluble guanylate cyclase (sGC) to NO by reducing the sGC heme iron, controlling cGMP production, arterial blood vessel tone, and blood pressure.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

"Administration" as used herein is inclusive of administration by another person to the subject or self-administration by the subject.

The term "alkoxy" refers to a straight, branched or cyclic hydrocarbon configuration and combinations thereof, including from 1 to 20 carbon atoms, preferably from 1 to 6 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; or hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl.

An "analog" is a molecule that differs in chemical structure from a parent compound, for example a homolog (differing by an increment in the chemical structure or mass, such as a difference in the length of an alkyl chain or the inclusion of one of more isotopes), a molecular fragment, a structure that differs by one or more functional groups, or a change in ionization. An analog is not necessarily synthesized from the parent compound. A derivative is a molecule derived from the base structure.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

The term "aralkyl" refers to an alkyl group wherein an aryl group is substituted for a hydrogen of the alkyl group. An example of an aralkyl group is a benzyl group.

"Aryl" refers to a monovalent unsaturated aromatic carbocyclic group having a single ring (e.g., phenyl) or multiple condensed or fused rings (e.g., naphthyl or anthryl), which can optionally be unsubstituted or substituted. A "heteroaryl group," is defined as an aromatic group that has at least one heteroatom incorporated within the ring or fused rings of the aromatic group. Examples of heteroatoms include, but are not limited to, nitrogen, oxygen, sulfur, and phosphorous. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The aryl or heteroaryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl or heteroaryl group can be unsubstituted.

The term "co-administration" or "co-administering" refers to administration of a compound disclosed herein with at least one other therapeutic or diagnostic agent within the same general time period, and does not require administration at the same exact moment in time (although co-administration is inclusive of administering at the same exact moment in time). Thus, co-administration may be on the same day or on different days, or in the same week or in different weeks. In certain embodiments, a plurality of therapeutic and/or diagnostic agents may be co-administered by combining the agents in a single dosage unit or form.

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

The terms "halogenated alkyl" or "haloalkyl group" refer to an alkyl group with one or more hydrogen atoms present on these groups substituted with a halogen (F, Cl, Br, I).

The term "hydroxyl" is represented by the formula —OH.

"Inhibiting" refers to inhibiting the full development of a disease or condition. "Inhibiting" also refers to any quantitative or qualitative reduction in biological activity or binding, relative to a control.

"N-heterocyclic" refers to mono or bicyclic rings or ring systems that include at least one nitrogen heteroatom. The rings or ring systems generally include 1 to 9 carbon atoms in addition to the heteroatom(s) and may be saturated, unsaturated or aromatic (including pseudoaromatic). The term "pseudoaromatic" refers to a ring system which is not strictly aromatic, but which is stabilized by means of delocalization of electrons and behaves in a similar manner to aromatic rings. Aromatic includes pseudoaromatic ring systems, such as pyrrolyl rings.

Examples of 5-membered monocyclic N-heterocycles include pyrrolyl, H-pyrrolyl, pyrrolinyl, pyrrolidinyl, oxazolyl, oxadiazolyl, (including 1,2,3 and 1,2,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), and dithiazolyl. Examples of 6-membered monocyclic N-heterocycles include pyridyl, pyrimidinyl, pyridazinyl, pyrazinyl, piperidinyl, morpholinyl, thiomorpholinyl, piperazinyl, and triazinyl. The heterocycles may be optionally substituted with a broad range of substituents, and preferably with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$alkyl)amino. The N-heterocyclic group may be fused to a carbocyclic ring such as phenyl, naphthyl, indenyl, azulenyl, fluorenyl, and anthracenyl.

Examples of 8, 9 and 10-membered bicyclic heterocycles include 1H thieno[2,3-c]pyrazolyl, indolyl, isoindolyl, benzoxazolyl, benzothiazolyl, benzisoxazolyl, benzisothiazolyl, benzimidazolyl, indazolyl, isoquinolinyl, quinolinyl, quinoxalinyl, purinyl, cinnolinyl, phthalazinyl, quinazolinyl, quinoxalinyl, benzotriazinyl, and the like. These heterocycles may be optionally substituted, for example with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$alkyl)amino. Unless otherwise defined optionally substituted N-heterocyclics includes pyridinium salts and the N-oxide form of suitable ring nitrogens.

The term "purified" does not require absolute purity; rather, it is intended as a relative term. Thus, for example, a purified peptide preparation is one in which the peptide or protein is more enriched than the peptide or protein is in its natural environment within a cell. For example, a compound preparation is purified such that the desired polysaccharide protein conjugate represents at least 50%, more particularly at least about 90%, and most particularly at least about 98%, of the total content of the preparation.

The term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

"Substituted" or "substitution" refers to replacement of a hydrogen atom of a molecule or an R-group with one or more additional R-groups. Unless otherwise defined, the term "optionally substituted" or "optional substituent" as used herein refers to a group which may or may not be further substituted with 1, 2, 3, 4 or more groups, preferably 1, 2 or 3, more preferably 1 or 2 groups. The substituents may be selected, for example, from $C_{1-6}$alkyl, $C_{2-6}$alkenyl, $C_{2-6}$alkynyl, $C3_8$cycloalkyl, hydroxyl, oxo, $C_{1-6}$alkoxy, aryloxy, $C_{1-6}$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, ar$C_{1-6}$alkyl, heterocyclyl and heteroaryl wherein each alkyl, alkenyl, alkynyl, cycloalkyl, aryl and heterocyclyl and groups containing them may be further optionally substituted. Optional substituents in the case N-heterocycles may also include but are not limited to $C_{1-6}$alkyl i.e. N—$C_{1-3}$alkyl, more preferably methyl particularly N-methyl.

A "therapeutically effective amount" refers to a quantity of a specified agent sufficient to achieve a desired effect in a subject being treated with that agent. For example, a therapeutically amount may be an amount of a CytB5R3 inhibitor that is sufficient to inhibit CytB5R3 activity in a desired cell in a subject. Ideally, a therapeutically effective amount of an agent is an amount sufficient to inhibit or treat the disease or condition without causing a substantial cytotoxic, or other substantially deleterious, effect in the subject. The therapeutically effective amount of an agent will be dependent on the subject being treated, the severity of the affliction, and the manner of administration of the therapeutic composition.

"Thiol" refers to the group —SH.

The term "substituted thiol" refers to a thiol group having the hydrogen replaced with, for example a $C_{1-6}$alkyl group ("—S($C_{1-6}$alkyl)"), an aryl ("—S(aryl)"), or an aralkyl ("—S(alkyl)(aryl)") and so on.

The term "thioalkyl" refers to an alkyl group wherein having at least one hydrogen replaced with thiol or substituted thiol.

"Treatment" refers to a therapeutic intervention that ameliorates a sign or symptom of a disease or pathological condition after it has begun to develop, or administering a compound or composition to a subject who does not exhibit signs of a disease or exhibits only early signs for the purpose of decreasing the risk of developing a pathology or condition, or diminishing the severity of a pathology or condition. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, $C_{1-4}$ alkyl, or $C_{1-4}$ alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. F or a general discussion of prodrugs involving esters see Svensson and Tunek, *Drug Metabolism Reviews* 165 (1988) and Bundgaard, *Design of Prodrugs*, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions that will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Pharmaceutical Compositions and Methods of Use

Disclosed herein are medical treatment methods and methods of use that involve the use of a compound, or a pharmaceutically acceptable salt thereof, having a structure of:

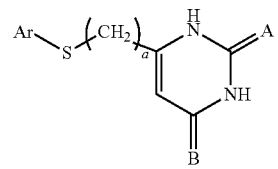

wherein A and B are each individually selected from O or S;

a is 1 to 4; and

Ar is optionally substituted aryl or optionally substituted heteroaryl.

In certain embodiments, A is S and B is O, or A is O and B is O, or A is O and B is S, or A is S and B is S.

In certain embodiments, a is 1.

In certain embodiments, Ar is phenyl or substituted phenyl having a structure of:

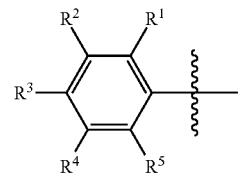

wherein $R^1$ to $R^5$ are each individually selected from H, optionally substituted alkyl (particularly lower alkyl), or halogen. In certain embodiments, $R^3$ is optionally substituted alkyl (particularly lower alkyl) or halogen; and $R^1$, $R^2$, $R^4$ and $R^5$ are each H. In certain embodiments, at least two of $R^1$ to $R^5$ are each individually selected from optionally substituted alkyl (particularly lower alkyl), or halogen. In certain embodiments, $R^1$ and $R^5$ are each individually selected from halogen, and $R^2$ to $R^4$ are each H. In certain embodiments, Ar is optionally substituted benzoxazole.

In certain embodiments, Ar is:

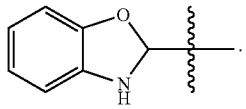

The compounds disclosed herein are CytB5R3 inhibitors.

In certain embodiments, acute administration of the compounds to a subject will result in increased blood flow and decreased blood pressure. In the acute administration embodiment, the compounds are vasodilators. Although not bound by any theory, it is believed that under acute administration conditions, the CytB5R3 inhibitors effect blood flow via regulation of the endothelial alpha globin heme iron redox state.

As used herein, "acute administration" means administering the compounds to a subject, or contacting the compounds with a cell containing or expressing CytB5R3, at a dosage of up to 50 μM of up to 24 hours. Such administration may range from continuous dosing for up to 24 hours or to a single dosage in a 24 hour. In any case, additional administration does not occur 24 hours after the initial dosage.

In certain embodiments, chronic administration of the compounds to a subject will result in decreased blood flow and increased blood pressure. In the chronic administration embodiment, the compounds are vasoconstrictors. Although not bound by any theory, it is believed that under chronic administration conditions, the CytB5R3 inhibitors effect blood flow via regulation of the sGC/cGMP pathway.

As used herein, "chronic administration" means administering the compounds to a subject, or contacting the compounds with a cell containing or expressing CytB5R3, at a dosage of up to 50 μM for a period of more than 24 hours. Such administration may range from dosing on consecutive days to an interval dosing schedule (e.g., days 1, 3, 5, 7, etc). In any case, additional administration occurs 24 hours after the initial dosage.

Reduced heme iron of soluble guanylyl cyclase (sGC), the nitric oxide (NO) receptor, is required to transduce the NO signal into the second messenger molecule cGMP. Disclosed herein for the first time it is shown that cytochrome B5 reductase 3 (CyB5R3) is an essential enzyme required to maintain sGC in the reduced state and increase cGMP following NO stimulation. Using genetic tools and novel pharmacological inhibitors of CyB5R3, a significant loss of nitric oxide stimulated cGMP is demonstrated. These effects are reversed when cells are treated with a heme independent activator of sGC, e.g., Bay-58-2267. In certain embodiments, inhibition of Cyb5R3 leads to sGC heme iron oxidation, resulting in sGC protein degradation, reduced cGMP signaling, impaired vascular reactivity and HTN. Furthermore, the point mutation T117S in Cyb5R3 associates with hypertension in the human population. Cyb5R3, by serving as an sGC heme iron reductase, regulates NO-sGC-cGMP signaling to control arterial vascular tone and blood pressure (see FIG. 1).

In certain embodiments, the compounds disclosed herein regulate arterial vascular tone and blood pressure. Disclosed herein are methods of regulating arterial vascular tone in a subject, comprising administering to a subject in need thereof, a therapeutically effective amount of a CytB5R3 inhibitor compound as disclosed herein. The subject may be selected as being amenable to treatment with a CytB5R3 inhibitor compound as disclosed herein.

Systemic hypertension (HTN) is a significant risk factor for cardiovascular disease and a major public health concern. A vast amount of clinical and experimental evidence indicates increased vasoconstriction as a result of dysfunctional nitric oxide (NO) signaling is a common pathogenic feature of HTN. The ability of NO to regulate the vasodilation of arterial blood vessels is well characterized in humans and experimental animal models. Arising from either endothelial or neuronal nitric oxide synthase (e/nNOS), NO elicits its biological actions in the vascular wall by binding to soluble guanylate cyclase (sGC) in VSM cells, which then converts guanosine triphosphate (GTP) to the second messenger molecule cGMP21-23. Termination of the cGMP-signaling cascade in VSMCs is catalyzed by phosphodiesterase 5 (PDE5). Three major intracellular effectors mediate the biological outcomes of increased cGMP in VSM cells: 1) cGMP-dependent kinases 2) cGMP-gated ion channels and 3) cGMP-regulated phosphodiesterases (PDEs). To date, a vast amount of clinical and experimental evidence has concluded that reduced NO bioavailability and/or lack of responsiveness to NO is a major contributing factor in the pathogenesis of HTN and cardiovascular disease. In the development of HTN, altered NO signaling has been suggested to occur on three levels: 1) eNOS uncoupling, leading to a reduction in NO bioavailability 24-26, 2) reactive oxygen species scavenge NO 27-29, also resulting in decreased NO bioavailability or 3) VSM cells fail to response to NO 30-34. Therapeutic options to overcome decreased NO bioavailability include organic nitrates (i.e. glyceryltrinitrate) and nitrovasodilator drugs, however, the use of these compounds is limited due to the lack of sufficient biometabolism, tolerance development and non-specific interactions of NO with biomolecules such as superoxide which results in peroxynitrite-mediated tyrosine nitration 35-37. To reduce these undesirable effects, compounds that directly stimulate heme dependent sGC (e.g. Riociguat), independent of NO, have gained tremendous appreciation for their potential to treat systemic and pulmonary hypertension as well as other cardiovascular related-diseases.

The major prerequisite for NO-induced sGC activation is reduced heme iron ($F^{2+}$) in sGC, as oxidation of sGC and the subsequent loss of heme completely abolish NO-induced, sGC-mediated cGMP production. sGC heme iron oxidation can be induced by several molecules, particularly superoxide and peroxynitrite, which are generated under conditions of oxidative stress. Once oxidized, sGC is prone to degradation via the ubiquitin protein degradation pathway. To circumvent the loss of cGMP levels in HTN, PDE 5 therapy (Tadalafil) has been tested, however, results showed mild to no improvement in lowering blood pressure in combination with antihypertensive therapies. This lack of improvement may be due oxidized sGC, which is unable to generate cGMP, therefore making PDE 5 therapy ineffective. Because of this, sGC activators such as Bay 58-2267 and its derivatives, compounds that activate oxidized heme or heme-deficient sGC, are affording new options for treating HTN and cardiovascular complications. In a recent phase II clinical trial for patients with acute decompensated heart failure, the sGC activator Bay 58-2667 caused a 16.6 mmHg decrease in systolic blood pressure. These data demonstrate that sGC targeted therapy could have potential benefits for treating HTN.

NADH cytochrome b5 reductase 3 or methemoglobin reductase is a flavoprotein known for its ability to transfer electrons from its NADH domain through cytochrome b5 (Cyb5) to an electron acceptor. Membrane restricted Cyb5R3 in somatic cells regulates several biological reduction reactions including elongation and unsaturation of fatty acids, cholesterol biosynthesis and drug metabolism, while the soluble form of Cyb5R3 resides in erythrocytes to reduce methemoglobin. In the human population, deficient Cyb5R3 activity leads to recessive hereditary methemoglobinanemia (RHM). Patients with type I RHM display mildly elevated methemoglobin levels in erythrocytes whereas patients with type II RHM suffer from severe developmental neurological disorders, shortened life span, and growth retardation due to decreased Cyb5R3 expression and/or activity in all somatic cells. It has recently been reported that decreased activity of Cyb5R3 in erythrocytes associates with hypertension. In the cardiovascular system, however, little is known about Cyb5R3. It has recently been reported that Cyb5R3 plays an important role in NO signaling within the endothelial cells of the vascular wall. Specifically, Cyb5R3 was shown to regulate the redox state of α globin in small artery and arteriolar endothelial cell. Through this α globin heme redox regulation process, it was found that Cyb5R3 controls NO diffusion to VSMCs and, as a result, modulates arterial vascular reactivity.

Currently, there are no published reports identifying a sGC reductase. However, it has now been discovered that Cyb5R3 is a sGC reductase. Accordingly, disclosed herein is a method for regulating sGC in a cell or a subject comprising administering to the cell or the subject a CytB5R3 inhibitor.

Disclosed herein is a method of administering the compound to a subject in need of, or has been recognized as being in need of, treatment with a CytB5R3 inhibitor. The subject may be selected as being amenable to treatment with a CytB5R3 inhibitor. A red blood cell based ferricyanide reduction assay could be used to test if there is increased activity of Cyb5R3. This assay, combined with common blood pressure analysis could be used to predict whether to give Cyb5R3 inhibitors.

In certain embodiments in which the compounds act as vasoconstrictors, the compounds may also increase thrombosis, increase proliferation, and/or increase inflammatory responses.

In certain embodiments in which the compounds act as vasoconstrictors, the compounds may be used for treating massive hemoptysis, GI bleed, epistaxis, migraine headache (post-prodome), musculoskeletal injuries in the acute phase, trauma, hemangioma repair and other intraoperative causes of excessive bleeding, bleeding diatheses, uterine hemorrhage or menorrhagia, septic shock, anaphylactic shock, or local role in agioedema, urticaria, and allergic rhinosinusitis.

In certain embodiments in which the compounds act as vasoconstrictors, the compounds may be co-administered with nitrite, nitrate, nitrodilator molecules, or 1H-(1,2,4) oxadiazolo(4,3-alpha)quinoxalin-1-one (ODQ), an inhibitor of sGC. In certain embodiments in which the compounds act as vasoconstrictors, the compounds may be co-administered with sGC activators such as, for example, cinaciguat (Bay-58-2267), riociguat (Bay-63-2521), Bay 41-8543, or Bay 41-2272. In such co-administration embodiments, the CytB5R3 inhibitors disclosed herein may be used for regulating blood pressure (e.g., preventing hypotension).

In certain embodiments in which the compounds act as vasodilators, the compounds may be used to achieve local vasodilation (e.g., for treating claudication, erectile dysfunction, myocardial infarction, musculoskeletal/sport injuries in the repair phase), to achieve systemic dilatation (e.g, for treating Raynaud's), or to achieve systemic arteriolar dilatation (e.g., for treating hypertension, diabetic vasculopathy, or cardiogenic shock).

Another aspect of the disclosure includes pharmaceutical compositions prepared for administration to a subject and which include a therapeutically effective amount of one or more of the compounds disclosed herein. The therapeutically effective amount of a disclosed compound will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed compounds is understood by those of skill in the art.

Pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical compositions disclosed herein include those formed from pharmaceutically acceptable salts and/or solvates of the disclosed compounds. Pharmaceutically acceptable salts include those derived from pharmaceutically acceptable inorganic or organic bases and acids. Particular disclosed compounds possess at least one basic group that can form acid-base salts with acids. Examples of basic groups include, but are not limited to, amino and imino groups. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid. In particular, suitable salts include those derived from alkali metals such as potassium and sodium, alkaline earth metals such as calcium and magnesium, among numerous other acids well known in the pharmaceutical art.

Certain compounds include at least one acidic group that can form an acid-base salt with an inorganic or organic base. Examples of salts formed from inorganic bases include salts of the presently disclosed compounds with alkali metals such as potassium and sodium, alkaline earth metals, including calcium and magnesium and the like. Similarly, salts of acidic compounds with an organic base, such as an amine (as used herein terms that refer to amines should be understood to include their conjugate acids unless the context clearly indicates that the free amine is intended) are contemplated, including salts formed with basic amino acids, aliphatic amines, heterocyclic amines, aromatic amines, pyridines, guanidines and amidines. Of the aliphatic amines, the acyclic aliphatic amines, and cyclic and acyclic di- and tri-alkyl amines are particularly suitable for use in the disclosed compounds. In addition, quaternary ammonium counterions also can be used.

Particular examples of suitable amine bases (and their corresponding ammonium ions) for use in the present compounds include, without limitation, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl) amine, 2-hydroxy-tert-butylamine, tris(hydroxymethyl) methylamine, N,N-dimethyl-N-(2-hydroxyethyl)amine, tri-(2-hydroxyethyl)amine and N-methyl-D-glucamine. For additional examples of "pharmacologically acceptable salts," see Berge et al., *J. Pharm. Sci.* 66:1 (1977).

Compounds disclosed herein can be crystallized and can be provided in a single crystalline form or as a combination of different crystal polymorphs. As such, the compounds can be provided in one or more physical form, such as different crystal forms, crystalline, liquid crystalline or non-crystalline (amorphous) forms. Such different physical forms of the compounds can be prepared using, for example different solvents or different mixtures of solvents for recrystallization. Alternatively or additionally, different polymorphs can be prepared, for example, by performing recrystallizations at different temperatures and/or by altering cooling rates during recrystallization. The presence of polymorphs can be determined by X-ray crystallography, or in some cases by another spectroscopic technique, such as solid phase NMR spectroscopy, IR spectroscopy, or by differential scanning calorimetry.

The pharmaceutical compositions can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the compound can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compound can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The compound can be combined with the base or vehicle according to a variety of methods, and release of the compound can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly (epsilon-caprolactone), poly(epsilon-aprolactone-CO-lactic acid), poly(epsilon.-aprolactone-CO-glycolic acid), poly (beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

The administration of the compound of the disclosure can be for either prophylactic or therapeutic purpose. When provided prophylactically, the compound is provided in advance of any symptom. The prophylactic administration of the compound serves to prevent or ameliorate any subsequent disease process. When provided therapeutically, the compound is provided at (or shortly after) the onset of a symptom of disease or infection.

For prophylactic and therapeutic purposes, the compound can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, dog, sheep, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to alleviate one or more symptoms of a targeted disease). In alternative embodiments, an effective amount or effective dose of the compound may simply inhibit or enhance one or more selected biological activities correlated with a disease or condition, as set forth herein, for either therapeutic or diagnostic purposes.

The actual dosage of the compound will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.01 mg/kg body weight to about 20 mg/kg body weight, such as about 0.05 mg/kg to about 5 mg/kg body weight, or about 0.2 mg/kg to about 2 mg/kg body weight.

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, intraosseous, or intranasal delivery versus intravenous or subcutaneous or intramuscular delivery. Dosage can also be adjusted based on the release rate of the administered formulation, for example, of an intrapulmonary spray versus powder, sustained release oral versus injected particulate or transdermal delivery formulations, and so forth.

The compounds disclosed herein may also be co-administered with an additional therapeutic agent. Additional agents for co-administration include, but are not limited to, an anti-inflammatory agent, an antimicrobial agent, a cytokine antagonist, an immunosuppressant, an anticancer agent, an anti-viral agent, a cytokine, a growth factor, an immunomodulator, a prostaglandin or an anti-vascular hyperproliferation compound.

The instant disclosure also includes kits, packages and multi-container units containing the herein described pharmaceutical compositions, active ingredients, and/or means for administering the same for use in the prevention and treatment of diseases and other conditions in mammalian subjects. Kits for diagnostic use are also provided. In one embodiment, these kits include a container or formulation that contains one or more of the compounds described herein. In one example, this component is formulated in a pharmaceutical preparation for delivery to a subject. The compound is optionally contained in a bulk dispensing container or unit or multi-unit dosage form. Optional dispensing means can be provided, for example a pulmonary or intranasal spray applicator. Packaging materials optionally include a label or instruction indicating for what treatment purposes and/or in what manner the pharmaceutical agent packaged therewith can be used.

EXAMPLES

Cyb5R3 associates with oxidized sGC in VSMs.

Figure 2:
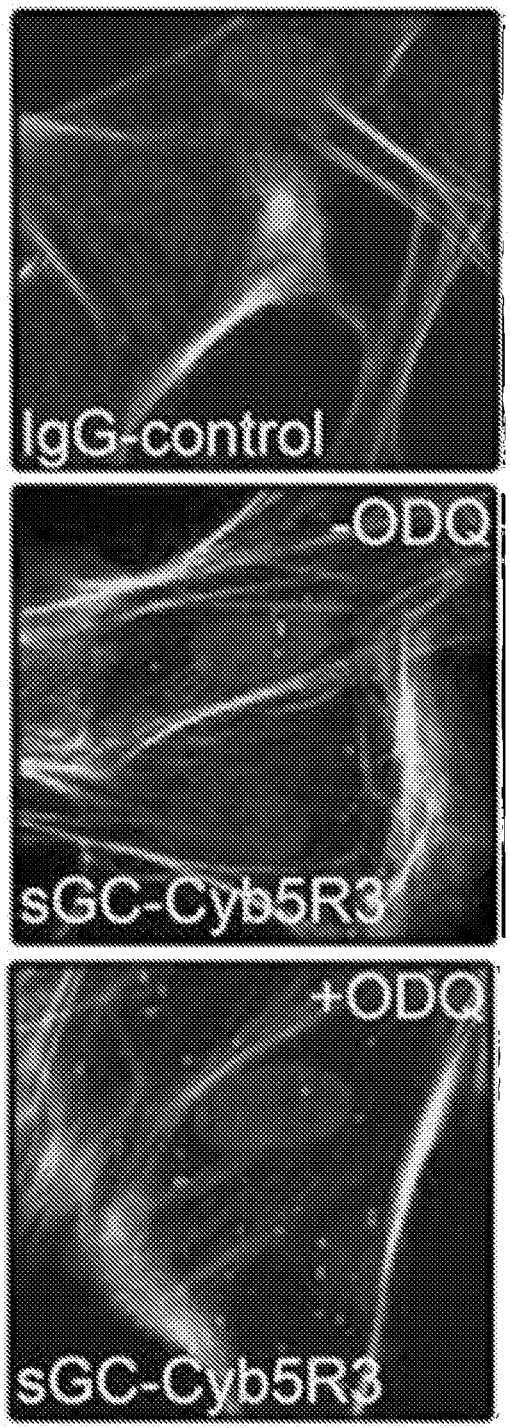
FIG. 2. Primary rat aortic vascular smooth muscle cells were treated with ODQ (10 µM, 10 min), washed with PBS and fixed paraformaldehyde. Cells were then subjected to a proximity ligation assay and imaged using confocal microscopy for sGC-Cyb5R3 macromolecular complexes (red punctates). Quantification of complexes per nuclei is shown in graph (n=3). **** indicates significance of <0.0001 and error bars are s.e.m.
Figure 2:
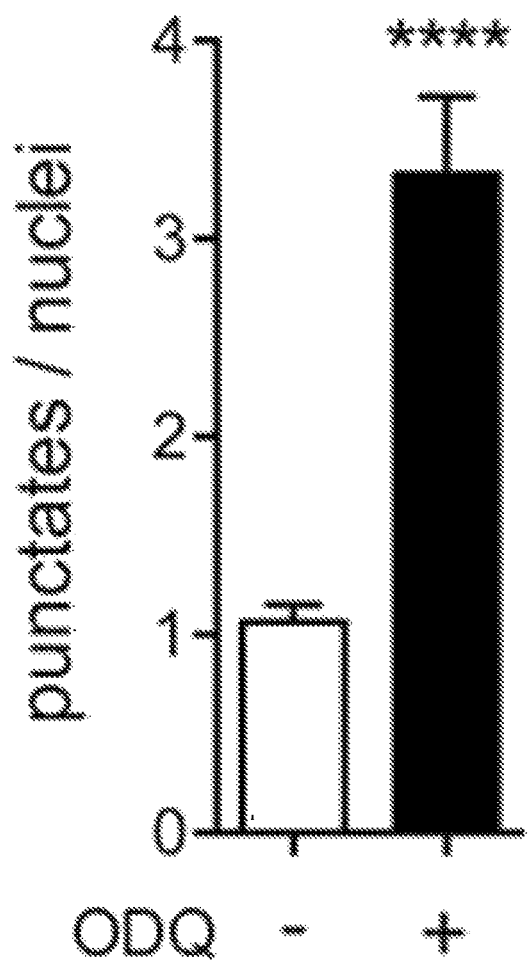

Studies were conducted using primary rat aortic VSMs exposed to the sGC oxidizing agent 1H-(1,2,4)oxadiazolo[4,3-a]quinoxalin-1-one (ODQ: 10 μM, 10 min). Following ODQ treatment, VSMs were fixed and subjected to a proximity ligation assay (PLA) to determine the association between oxidized sGC and Cyb5R3. Results demonstrate that exposure to ODQ increases number of macromolecular complexes (FIG. 2), suggesting that Cyb5R3 increases its association with sGC when oxidized.

Purified Cyb5R3 directly reduces oxidized sGC resulting in increased NO-induced cGMP production.

Figure 3:
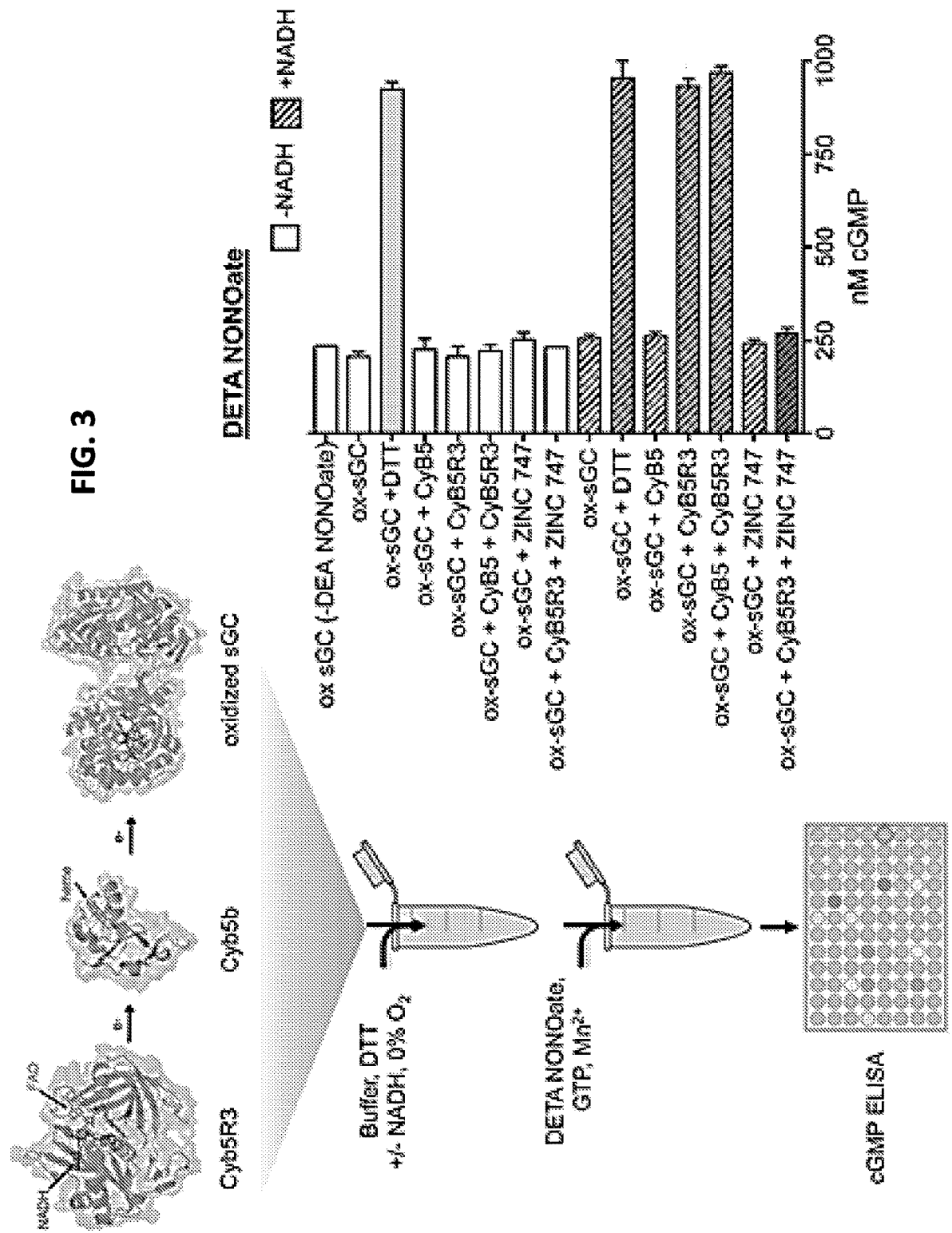
FIG. 3. Purified Cyb5R3 directly reduces oxidized sGC resulting in increased NO-induced cGMP production. Purified Cyb5R3, Cyb5b and oxidized sGC were combined and incubated in 50 mM trienthanolamine buffer, 1 mM DTT (positive control), 30 µM ZINC 747 (Cyb5R3 inhibitor), +/−10 µM NADH (required co-factor for Cyb5R3) in the absence of oxygen. Samples were then combined with GTP (1 mM), and Mn$^{2+}$ (1 mM) followed by stimulation with 100 µM DETA NONOate (NO donor). After 5 min, reactions were stopped and samples were measured for cGMP. Quantification of cGMP results is shown in the graph (right) (n=2). Error bars are s.e.m.

To test if Cyb5R3 and its protein partner Cyb5b can directly regulate sGC reduction and sensitize sGC to NO, purified proteins were generated. Following protein purification, samples were subjected to an in vitro NO-cGMP assay (experimental details are in FIG. 3 legend). Results from this study reveal that Cyb5R3 sensitizes sGC to NO resulting in augmented production of cGMP (FIG. 3). Surprisingly, this reaction does not require Cyb5. These results show redox dependency since cGMP production is NADH dependent and blocked using ZINC 747, an inhibitor that binds the NADH pocket of Cyb5R3. Together, these results suggest that Cyb5R3 directly reduces oxidized sGC and making it sensitive NO.

Purified Cyb5R3 directly reduces oxidized sGC and limits sGC activation with Bay-58-2667.

Figure 4:
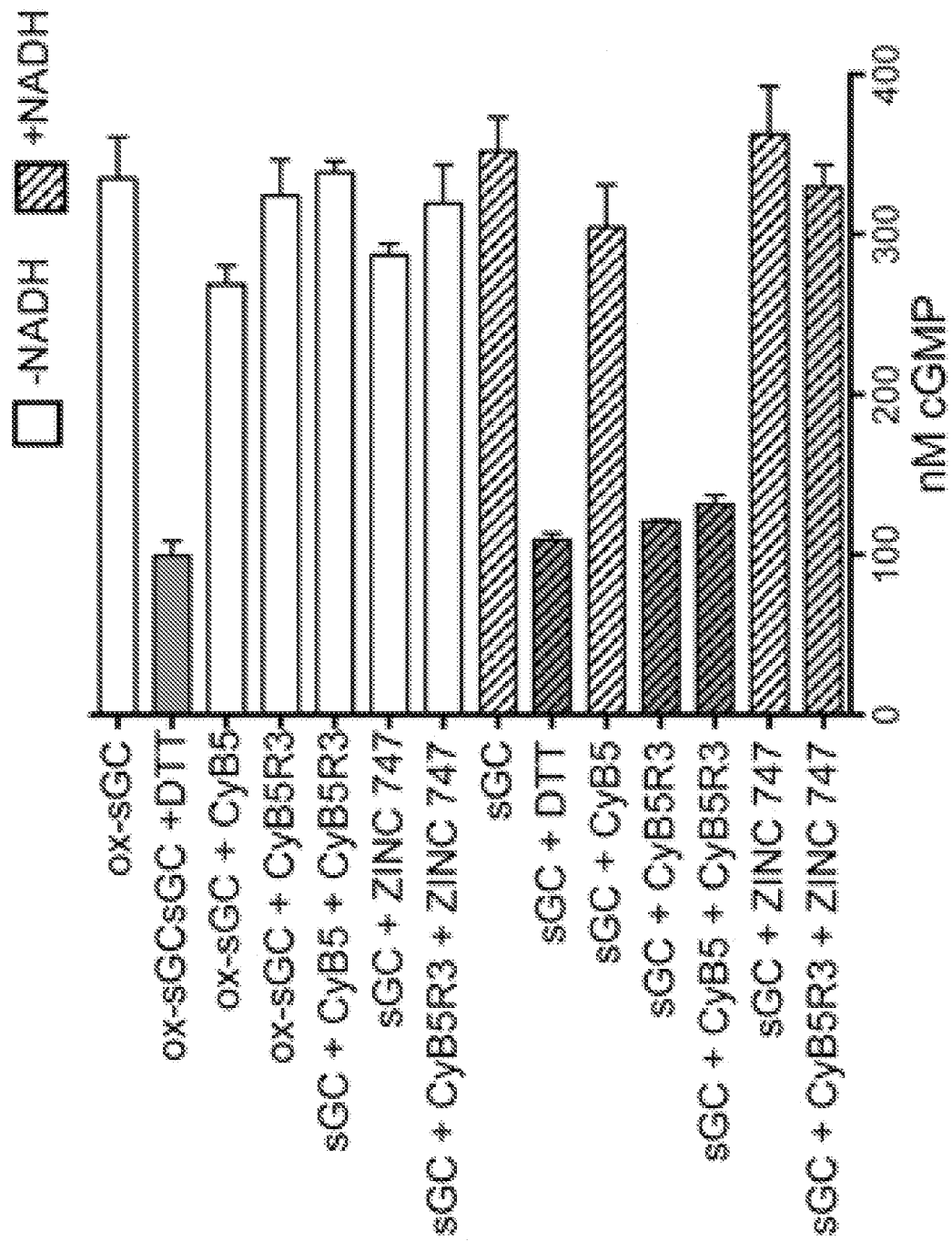
FIG. 4. Purified Cyb5R3 directly reduces oxidized sGC resulting in limited stimulation by the sGC activator Bay 58-2667. Purified Cyb5R3, Cyb5b and oxidized sGC were mixed and incubated in trienthanolamine buffer, DTT (positive control), ZINC 747 (Cyb5R3 inhibitor), +/−NADH (required co-factor for Cyb5R3) in the absence of oxygen. Samples were then combined with GTP, and Mn$^{2+}$ followed by stimulation with 100 nM Bay 58-2667. After 5 min, reactions were stopped and samples were measured for cGMP. Quantification of cGMP is shown in the graph (n=2). Error bars represent s.e.m.

Using identical experimental conditions as shown in FIG. 3, NO was replaced with Bay 58-2667, which specifically activates sGC in its oxidized or heme deficient state. Our results demonstrate Bay 58-2667 does not increase cGMP production in the presence of Cyb5R3 and does not require Cyb5 (FIG. 4). These data are consistent with data in FIG. 3, whereby Cyb5R3 can directly reduce oxidized sGC making it sensitive to NO but not Bay 58-2667.

Figure 5:
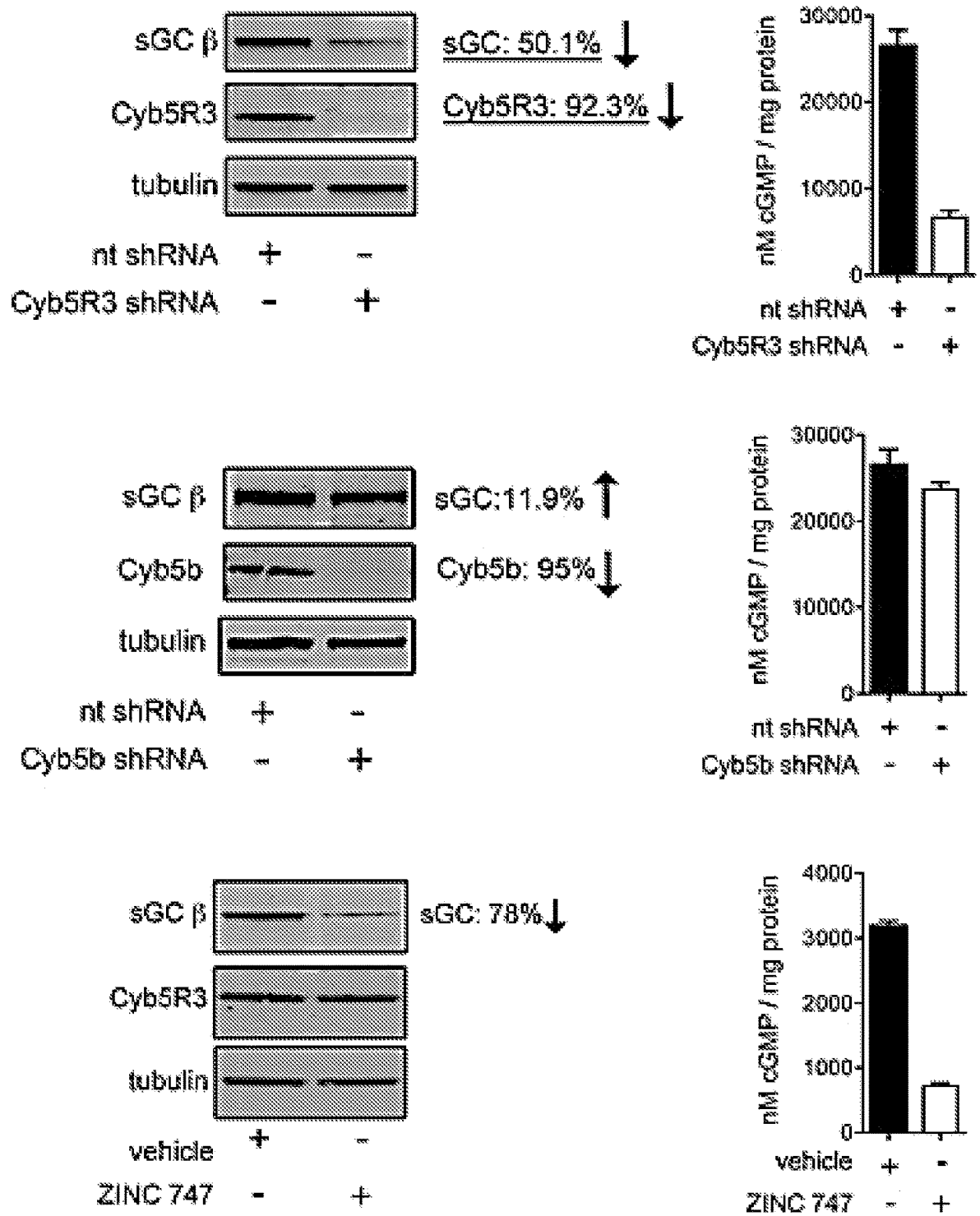
FIG. 5. Loss of Cyb5R3 protein or activity, but not Cyb5b, causes sGC protein degradation and decreased basal sGC expression. Primary rat aortic VSMs were transduced with lentivirus to express non-targeting, Cyb5R3 and Cyb5b shRNA (seven days) or to ZINC 39395747 (30 µM, 24 hrs). Cells were lysed for protein and measured for sGC, Cyb5R3, Cyb5b and tubulin expression. In addition, cells were treated with sildenafil (1 µM, 18 hrs) to measure basal cGMP production (n=3). Error bars represent s.e.m.

Non-targeting (NT), Cyb5R3 and Cyb5b shRNA lentiviruses were generated for protein knockdown. Using this approach, <90% knockdown for both Cyb5R3 and Cyb5b was achieved in rat aortic VSMs. Since sGC oxidation results in sGC protein degradation, a Western blot analysis from knockdown cells was performed. Interestingly, a 50% decrease in sGC expression was observed which resulted in 50% decrease basal cGMP production (FIG. 5). Consistent with the purified protein data, we did not observe loss of sGC protein with Cyb5b knockdown (FIG. 5). Pharmacological inhibition of Cyb5R3 with ZINC39395747 also resulted in decrease in sGC protein (<75%) and basal cGMP levels (FIG. 5).

Figure 6:
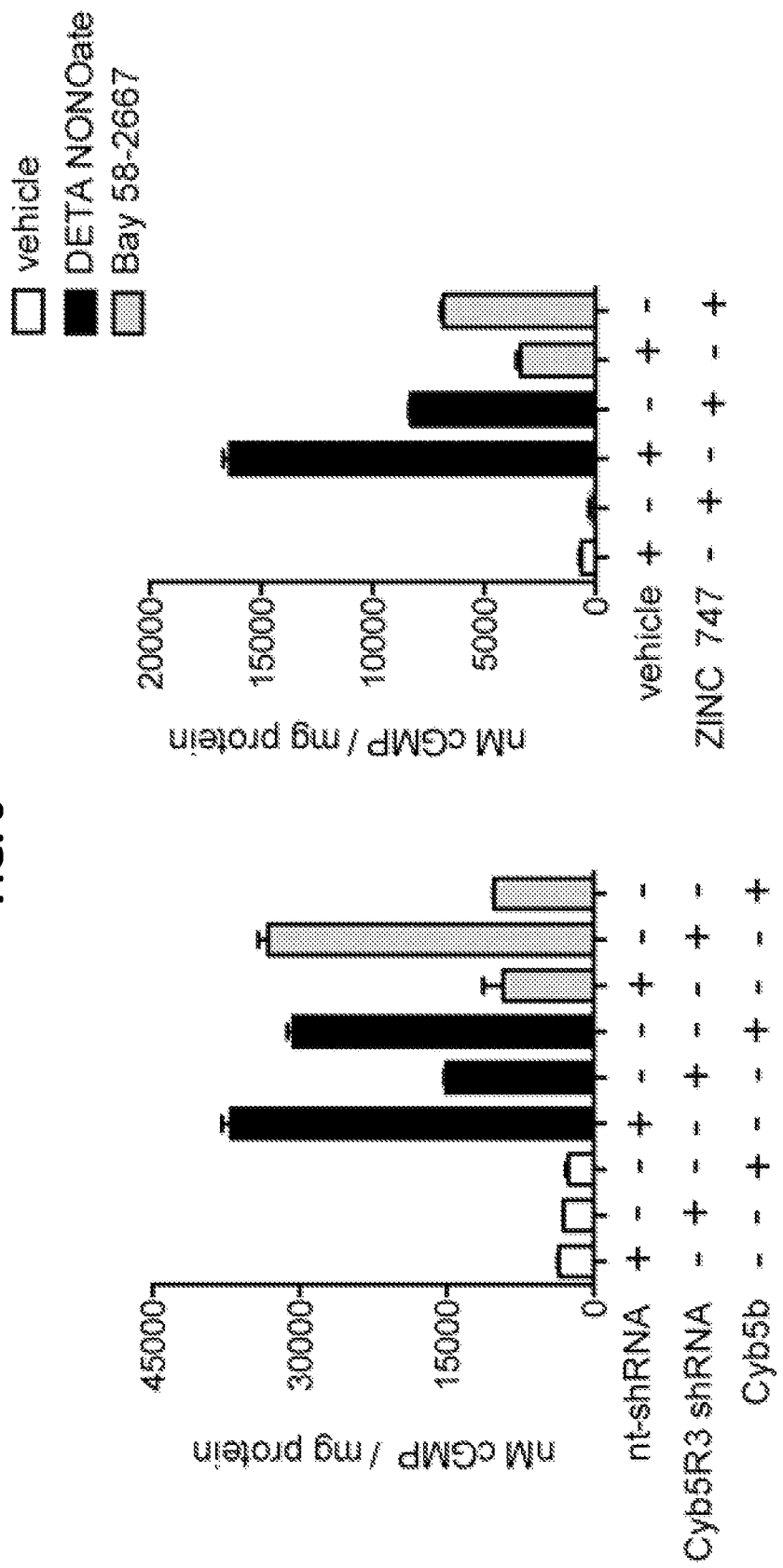
FIG. 6. Loss of Cyb5R3 or inhibition of Cyb5R3 activity causes decreased cGMP following NO stimulate and increased cGMP following Bay 58 2667 treatment. cGMP production in primary rat VSMs treated with and without DETA NONOate or Bay 58-2667 following Cyb5R3 knockdown or with ZINC 39395747. Quantification of cGMP is shown in the graph (n=2). Error bars represent s.e.m.

Whether genetic loss or pharmacological inhibition of Cyb5R3 altered NO-induced cGMP production in rat aortic VSMs was tested. Results shown in FIG. 6 demonstrate that loss of Cyb5R3 protein and activity causes a ~60% decrease in cGMP production when stimulated with the NO donor DETA NONOate. However, genetic loss of Cyb5b showed little effect.

Figure 7:
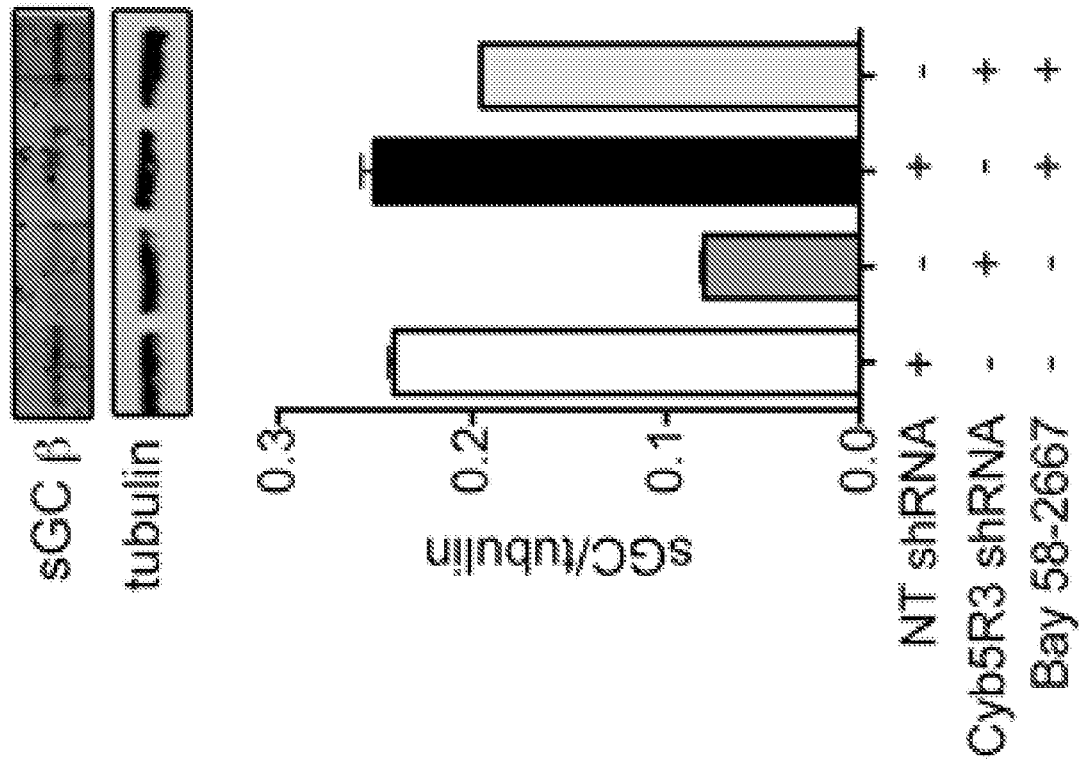
FIG. 7. Bay 58-2667 rescues sGC protein degradation following Cyb5R3 knockdown or activity inhibition. a, Western blot analysis for sGC expression in primary rat VSMs treated with and without Bay 58-2667 following Cyb5R3 knockdown or with ZINC 39395747 (b). Quantification of sGC expression is shown in the graph below (n=2). Error bars represent s.e.m.
Figure 7:
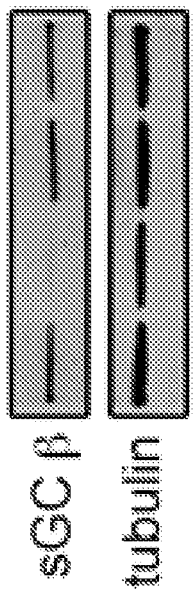
Figure 7:
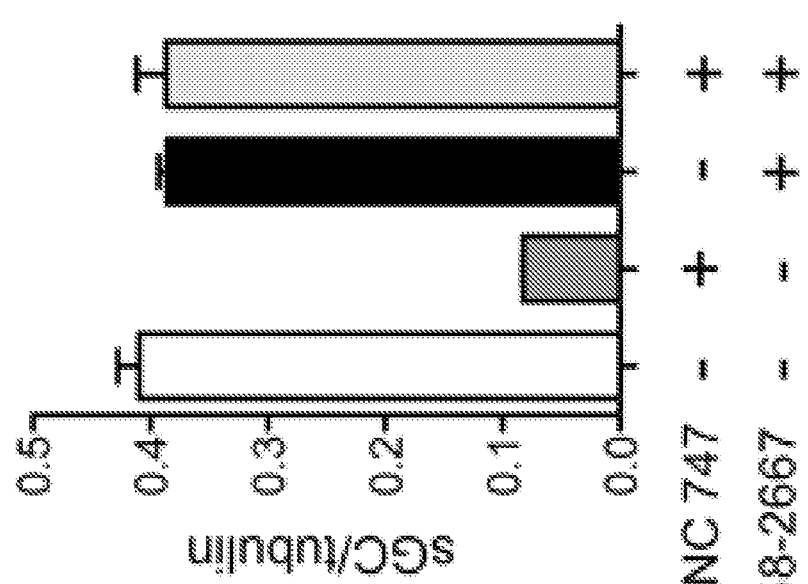

Previous reports demonstrated that the sGC activator, Bay 58-2667 prevents sGC proteasome degradation and increases cGMP production. It was therefore tested if Bay 58 2667 could rescue the effects caused by decreased Cyb5R3 expression and activity. Shown in FIG. 7, restoration of sGC protein levels in Cyb5R3 knockdown or ZINC 747 VSMs when treated with Bay 58 2667 was observed.

Figure 8:
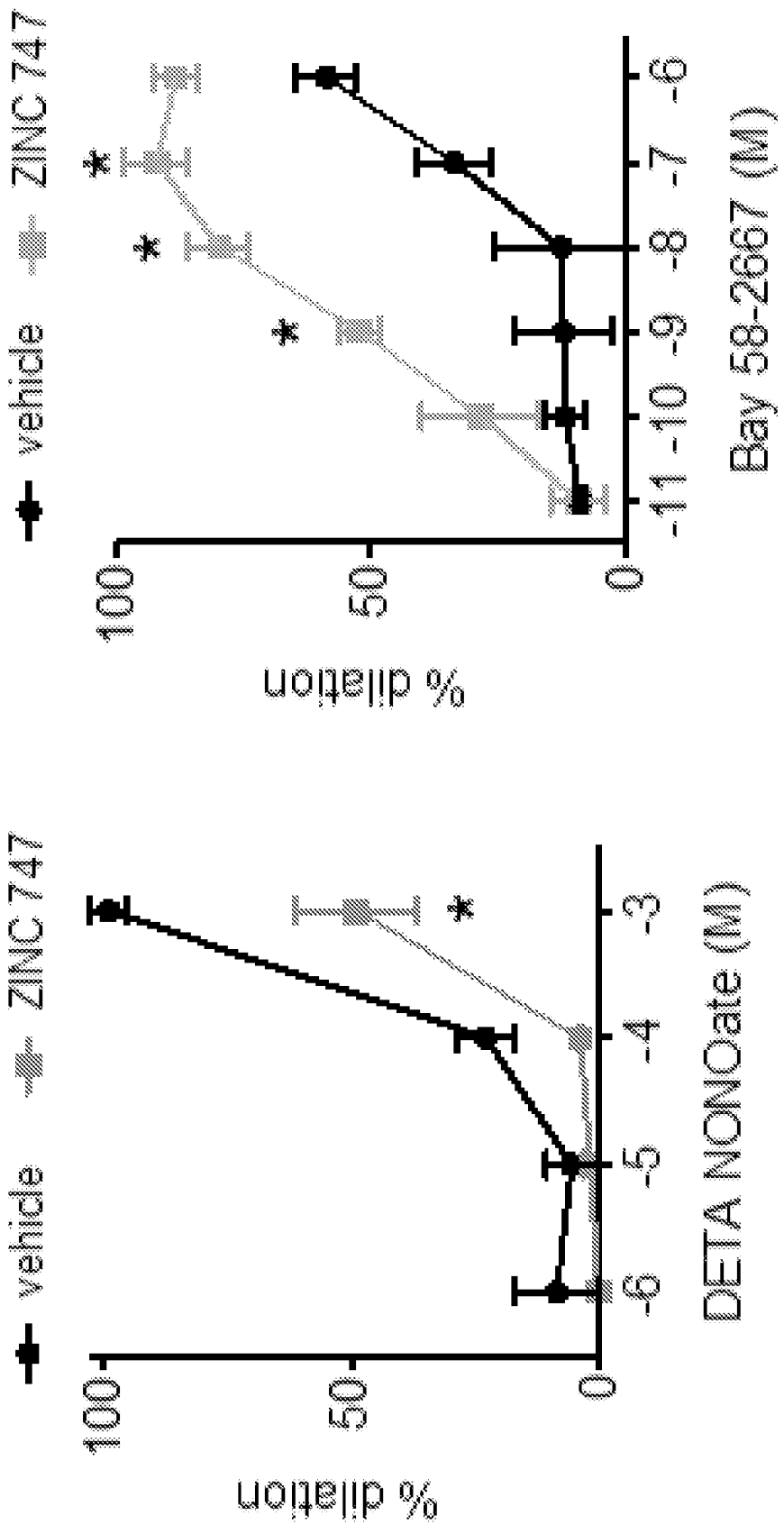
FIG. 8. Dose response curves to DETA NONOate and Bay 58-2667 on thoracodorsal arteries following treatment with ZINC 39395747. Isolated thoracodorsal arteries were pre-treated for 24 hours with ZINC 39395747 followed by cumulative dose responses to DETA NONOate for Bay 58-2667 using pressure myography (n=3). Error bars represent s.e.m.

To examine the functional role of Cyb5R3 activity, thoracodorsal arteries (internal diameter of 225 μm) were incubated with ZINC 39395747 for 24 hrs and pressure myography was performed. Results from these studies demonstrate an inhibited dose response the NO donor DETA NONOate and an augmented vasodilatory dose response with Bay 58-2667 (FIG. 8). These results are consistent with cell culture data suggesting that CyB5R3 is critical for sGC heme redox regulation.

Figure 9:
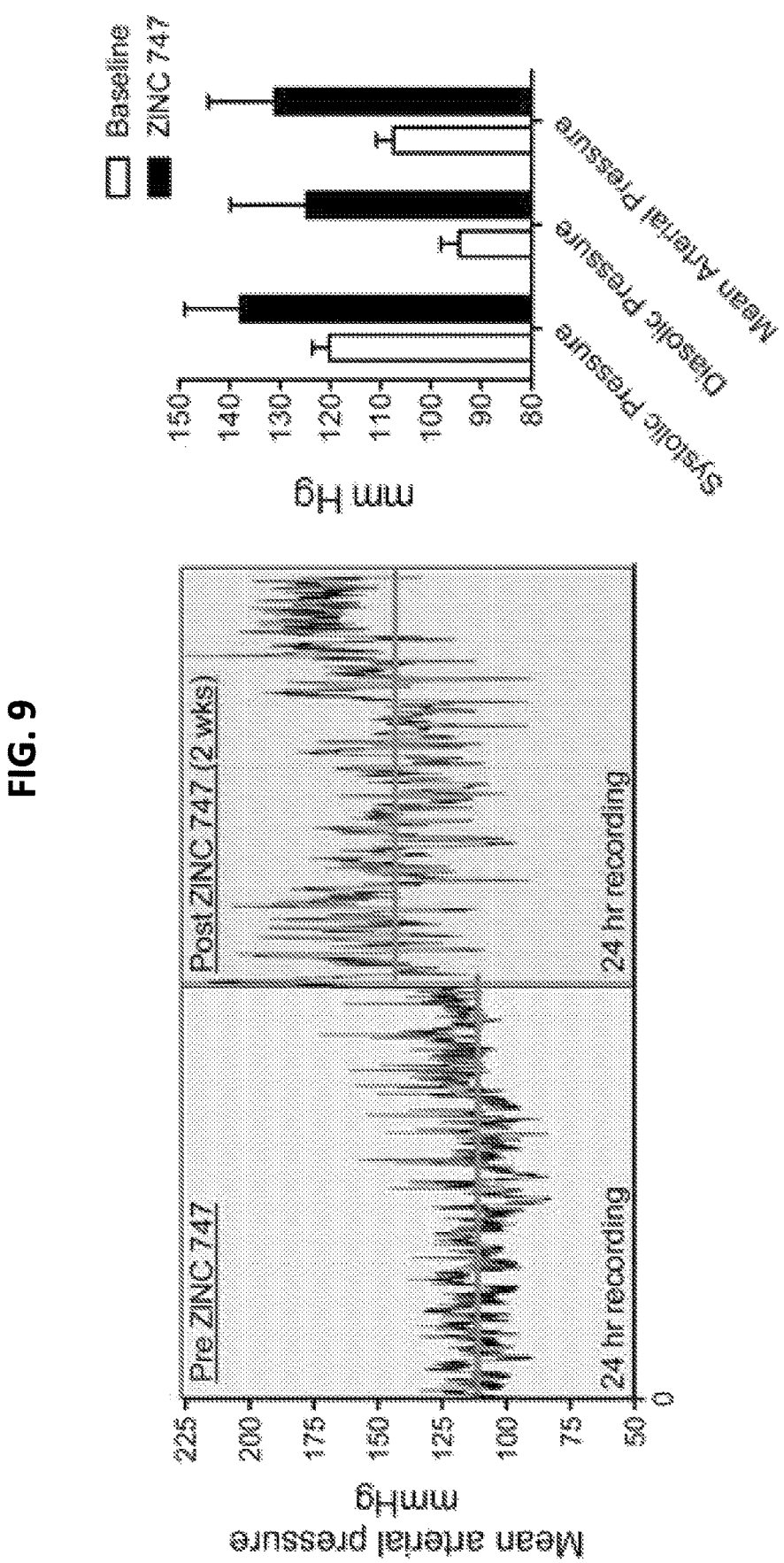
FIG. 9. Blood pressure analysis in conscious mice using radio telemetry pre- and post-infusion of ZINC 39395747. C57B1/6 were implanted with radio transmitters followed by implantation of osmotic mini pumps delivering 10 mg/kg/day of ZINC 39395747. Tracings on the left show a representative animal pre ZINC 39395747 infusion and post ZINC 39395747 infusion. The graph on the right shows systolic, diastolic and mean arterial pressure pre and post ZINC 39395747 infusion (n=2). Error bars represent s.e.m.

Studies were performed on C57B1/6 mice implanted with radio transmitters to measure systemic blood pressure in conscious mice, followed by implantation of osmotic mini pumps, which delivered 10 mg/kg/day of ZINC 747. Shown in FIG. 9, 14-day administration of ZINC 39395747 causes hypertension with increases in mean arterial pressure, systolic pressure and diastolic pressure. Furthermore, thoracodorsal arteries show smooth muscle cell hypertrophy.

Docked Model

This model was refined by analysis of Cyb5R3 crystal structures in the RCSB Protein Data Bank (PDB IDs: 1QFY and 1UMK). These are crystal structures of Cyb5R3 and a close homolog that contain the cofactor FAD, 1QFY also contains its substrate NADH. Superposition of propylthiouracil on the NADH ring followed by energy minimization with Smina, a fork of AutoDock Vina that is customized to better support scoring function development and high performance energy minimization led to the proposed position of PTU in the NADH pocket of Cyb5R3.

Small Molecule Selection

After establishing this model, a thiouracil-based pharmacophore screening of the commercially available compounds in the ZINC database was performed. The resulting pharmacophore-aligned compounds were energy minimized and scored using smina with the default AutoDock Vina scoring function against the receptors 1UMK and 1QFY. The receptor structures were prepared using the prepare_receptor.py script from AutoDockTools. The best ranking molecules were reviewed and chosen based on chemical diversity and potential interactions. For the follow-up assay, a selection was made of compounds that were chemically similar to the most potent inhibitor, ZINC05626394, which was achieved by performing a 70% similarity search of the ZINC database. The compounds were selected based on desired substituents for a detailed structure and activity relationship (SAR).

Cloning, Expression, and Purification of Human Cytochrome $b_5$ Reductase

Purified proteins were prepared as previously described in Sparacino-Watkins et al. Briefly, human Cyb5R3 gene was cloned into the pET28a plasmid containing a His$_6$ tag on the N-terminus of Cyb5R3. The plasmid was transformed into SoluBL21 cells (Genlantis) and protein purification was carried out as previously described. Spectrophotometric measurements were performed with a Cary 50 spectrophotometer and concentrations of Cyb5R3 were measured with UV-VIS spectroscopy using the previously published extinction coefficients for Cyb5R3 ($\varepsilon^{462\ nm}$=10.4 mM$^{-1}$·cm$^{-1}$). Chromatographic separation was conducted with an Äkta-Purifier FPLC (GE Healthcare Life Sciences, USA) running Unicorn software version 5.1. Metal affinity chromatography resin, Ni-NTA superflow (Qiagen), was packed into a XK 26/20 column (GE). Protein identity was confirmed with liquid chromatography and tandem mass spectrometry (LC-MS/MS, University of Pittsburgh Genome and Protein Core Facilities).

Inhibition Assay

The NADH-ferricyanide reductase activity for purified Cyb5R3 was assayed by spectrophotometric measurements using the rate of potassium ferricyanide reduction at 420 nm, according to Strittmatter and Velick. The assay mixture contained 0.1 M potassium phosphate buffer, pH 7.5 containing 10 mM potassium ferricyanide, 5 mM NADH and 90 nM of purified Cyb5R3 in a final volume of 1 mL. The reaction was started by addition of cofactor NADH and reduction of ferricyanide was followed for 2 min by recording the absorbance decrease at 420 nm using Cary 50 spectrophotometer and small glass cuvettes with a 0.2 cm path length. Since NADH has partial reduction power independent of Cyb5R3, the reaction rate was corrected by subtracting the reaction rate of ferricyanide in the absence of enzyme. The enzyme activity was calculated using the extinction coefficient of 1.02 mM$^{-1}$ cm$^{-1}$ for the difference in absorbance between reduced and oxidized form of ferricyanide.

In order to observe the inhibitory effect of each Cyb5R3 small molecule inhibitor, the compounds were pre-incubated with Cyb5R3 at 37° C. for 15 minutes followed by measurements in NADH-ferricyanide reductase activity as described above. For primary screening, 500 μM of each compound was used and compounds that gave 100% inhibition of CyB5R3 were selected for a secondary screen where 50 μM of each compound was tested. Finally, compounds active in this secondary screen were evaluated at different concentrations and IC$_{50}$ values were calculated using GraphPad Prism software by linear fit.

In Vitro Cyb5R3 Activity Assay:

Cyb5R3 activity was determined according to the method by Siendones et al, 2014 with modifications. In brief, human embryonic kidney cells were plated in 6-well plates and treated with 21.86 μM of ZINC05626394, 36.82 μM of ZINC39395747 and 30.16 μM of ZINC0562626 for 24 hrs. Following treatment, cells were washed two times with PBS, trypsinied and centrifuged at 1000 g for 5 min to pellet cells. The pellet was resuspended in 500 μl of buffer A (130 mM Tris-HCl pH7.6, 0.1 mM DTT and 1× protease inhibitor cocktail). Lysates were homogenized with a micro pestle and centrifuged at 2000 g for 10 min at 4° C. and the supernatant was collected. To test for Cyb5R3 activity, 30 μg of total lysate was incubated with 1 mM Tris-HCl pH 7.6, 0.5 mM EDTA, 2 mM potassium ferricyanide and 0.25 mM NADH for 2 min at room temperature. During the reaction, absorbance changes at 420 nm were measured to determine ferricyanide reduction by CyB5R3.

To confirm specificity of the Cyb5R3 activity assay, Cyb5R3 stable knockdown HEK cells were generated with lentivirus. The shRNA construct was purchased from Sigma (TRCN0000236407). The ViralPower Lentiviral Expression System (Invitrogen) was used to generate lentivirus with the following modifications. For transfection, two mixtures of reagents were prepared. Mix 1 contained 5.6 μg of pLP1, 2.4 μg of pLP2, 4 μg of pLP/VSVG and 10 μg of pLKO.1-Cyb5R3 shRNA in 0.5 mL of Optimem medium. Mix 2 contained 50 μL lipofectamine in 0.5 mL of Optimem, which was incubated for 5 minutes at room temperature (RT). Next, the two mixtures were combined for 20 minutes at RT then added dropwise to HEK 293FT cells grown to 90-95% confluency in 10 cm$^2$ dish. After 5 hours, media was replaced with Freestyle 293 plus 5% penicillin/streptomycin. After 72 hrs days of culture, viral supernatant was collected and centrifuged at 1000 rpm for 5 minutes to pellet cell debris. Viral supernatant was then concentrated using an Amicon Ultra-15 filter unit with a 100 kDa MWCO. For lentivirus transduction, 20 ul of concentrated virus was added to HEK 293 cells at 50% confluency in 35 $mm^2$ dish with 10 ug/ml polybrene. Twenty-four hours after transduction, cells were selected for 10 days with 1 μg/mL of puromycin to generate stable Cyb5R3 knockdown cells.

Results and Discussion

Docked Model

Figure 10:
FIG. 10. Molecular structure of Cyb5R3. Cyb5R3 consists of two domains: the FAD-binding domain (Thr30-Ser145, blue) and a NADH-binding domain (Ser173-Phe300, red). These domains are connected by a linker (hinge) at the bottom (Gly146-Lys172, purple), which allow the domains to move away and towards each other.
Figure 11A:
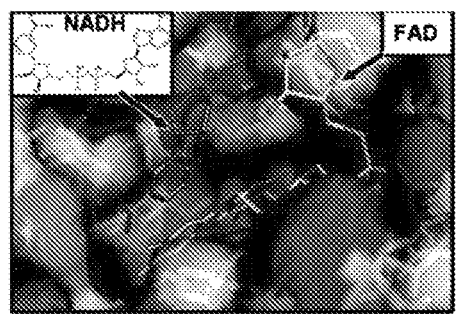
FIG. 11. Flow chart representing the approach taken to identify new small molecule inhibitors for Cyb5R3. a, shows the NADH and FAD binding domain of CytB5R3 and b illustrates the proposed binding of PTU in the NADH binding pocket. c, shows the structure of PTU and an example of a carbon tail modification. d, represents an example (ZINC 39395747) of a modification to that carbon tail that is predicted to increase the binding affinity to the NADH pocket.
Figure 11B:
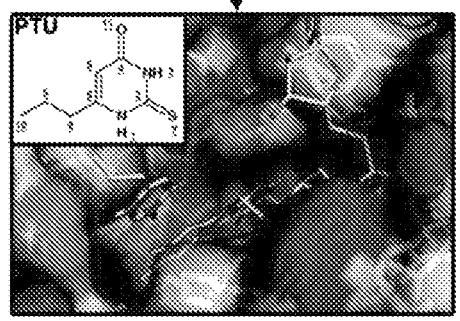
Figure 11C:
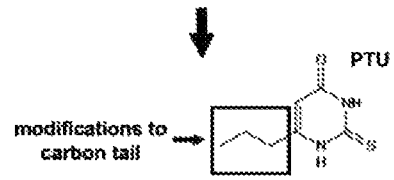
Figure 11D:
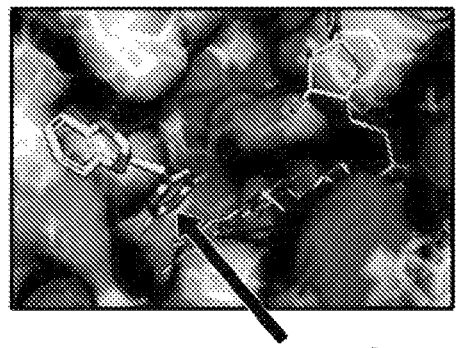
Figure 11D:
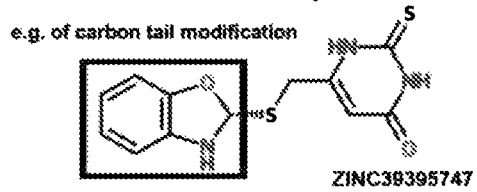

Cyb5R3 contains a flavin adenine dinucleotide (FAD) as a noncovalently bound cofactor. FAD facilitates electron transfer processes where its isoalloxazine ring can accept electrons at different positions. Oxidized FAD-bound Cyb5R3 uses two electrons from NADH through hydride transfer to fully reduce FAD in order to transfer single electrons to acceptors such as methemoglobin. The docked model intervenes at the initiation of this process where NADH acts as the initial electron donor. As shown in FIG. 10, Cyb5R3 consists of two domains with the bound FAD cofactor (orange), a FAD-binding domain (Thr30-Ser145, blue) and a NADH-binding domain (Ser173-Phe300, red). These domains are connected by a linker (hinge) sequence at the bottom (Gly146-Lys172, purple), which allow the domains to move away and towards each other (PDB id 1UMK). There are no crystal structures of human Cyb5R3 that contain NADH, therefore NADHs binding mode was obtained by analysis and alignment of the homolog with human Cyb5R3. This method provided a suggested binding mode for NADH at its corresponding binding site in Cyb5R3.

Due to the molecular structure of PTU and NADH, we hypothesized that PTU competes for binding at the NADH site in order to inhibit Cyb5R3 activity. Docking of PTU in the NADH site using smina led to the proposed binding model for thiouracil as presented in FIG. 11. It was rationalized that thiouracil binds to the NADH site of the protein where it stacks with the isoalloxazine rings, which are similar to the stacking arrangements of NADH. This binding mode allows for four specific interactions between PTU and the binding pocket, namely; O11 accepts a hydrogen from Thr181 side chain OH, N3 donates a hydrogen to Thr184 side chain OH, S7 accepts hydrogen from terminal OH of Phe300 and N1 donates hydrogen to the terminal carbonyl of Phe300.

Pharmacophore Screening and Inhibition Assay

Figure 12:
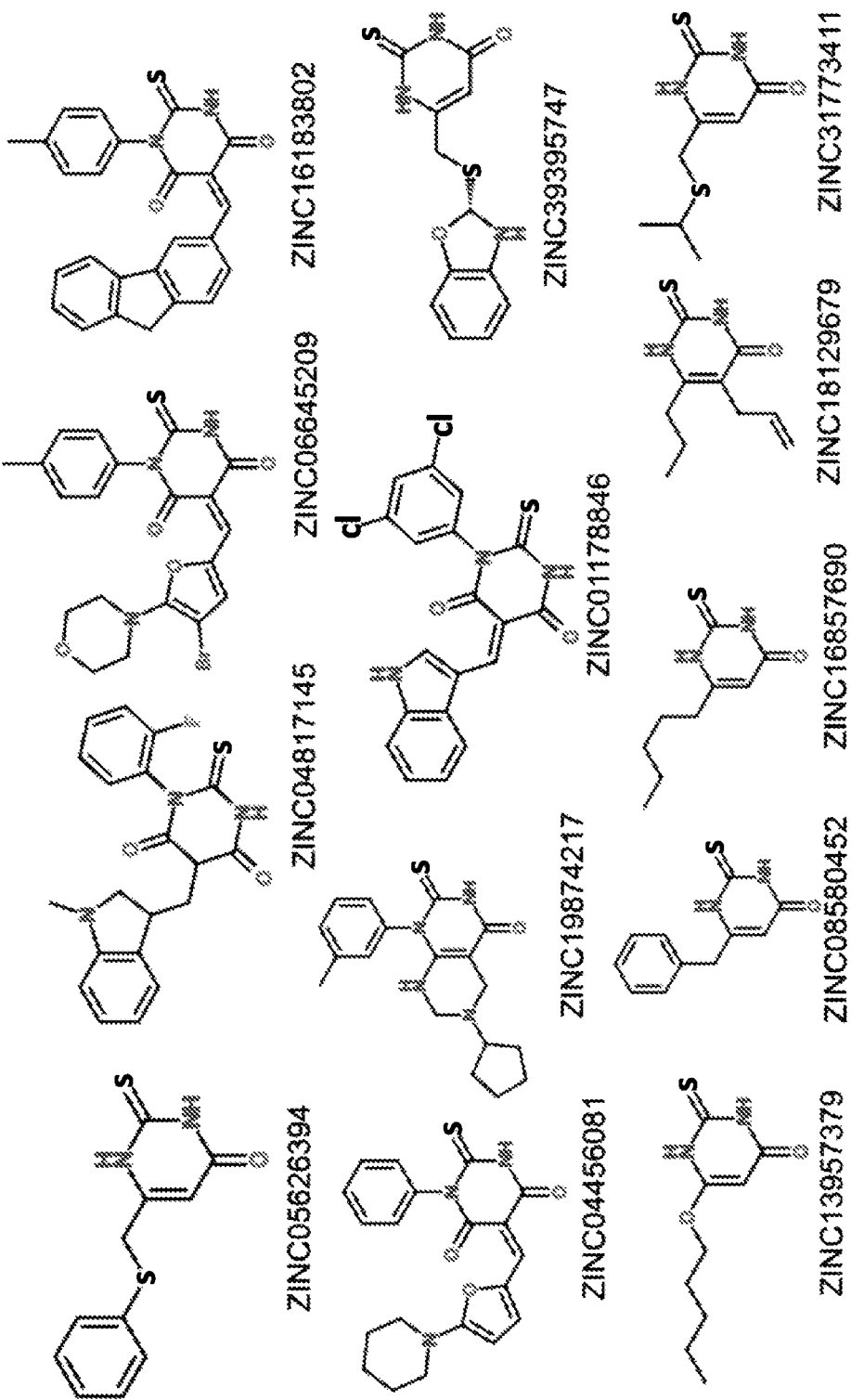
FIG. 12. List of ZINC compounds identified through thiouracil-biased pharmacophore screening. Structures show modified carbon tail and side chain modifications to parent thiouracil compound.
Figure 13:
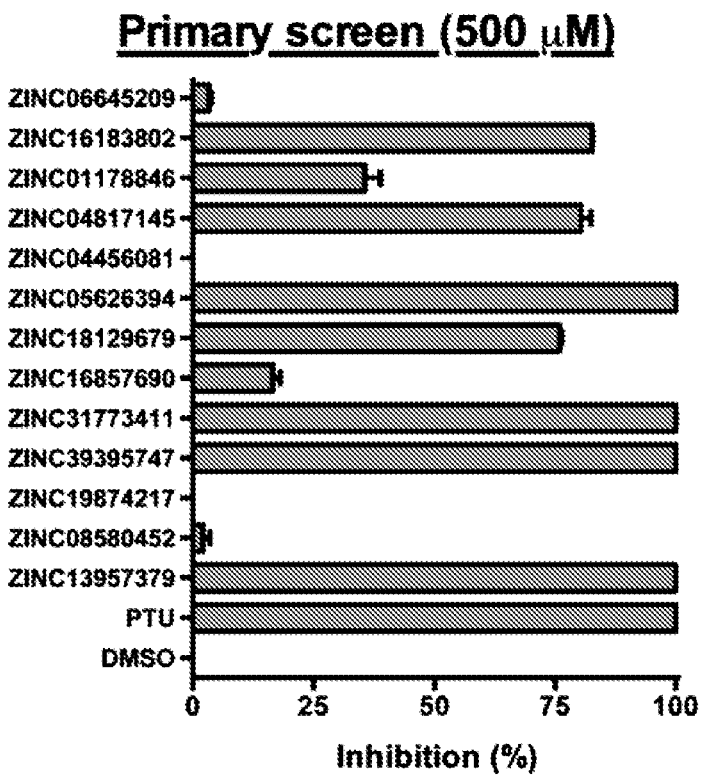
FIG. 13. Primary screening, secondary screening and $IC_{50}$ values of identified compounds. Primary screen using purified human CyB5R3 was incubated with each compound (500 μM) followed by activity measurements with an NADH-ferricyanide reductase assay. Of the 4 compounds that gave 100% inhibition, a secondary screen was used with 50 μM concentrations. Two compounds were identified, ZINC39395747 and ZINC05626394. The calculated IC-50s were 10.84 μM and 18.41 μM, respectively.
Figure 13:
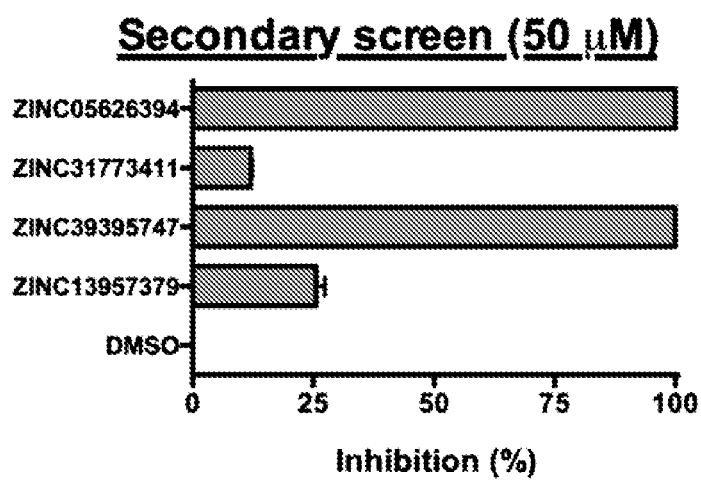
Figure 13:
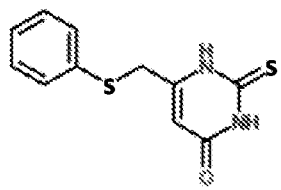
Figure 13:
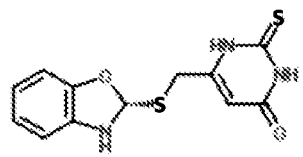

After establishing this model, a thiouracil-based pharmacophore screening of commercially available compounds in the ZINC database was performed using the ZincPharmer server. The resulting compounds were energy minimized and scored against the receptors 1UMK and 1QFY and the best ranking molecules were reviewed and chosen based on chemical diversity and predicted interactions. For the initial screen, 13 commercially available compounds (FIG. 12) were tested in the assay and results are shown and compared to PTU in FIG. 13. In the primary screen, 13 compounds were used at a concentration of 500 μM, which revealed 4 compounds, ZINC05626394, ZINC31773411, ZINC39395747 and ZINC13957379, exhibiting 100% inhibition similar to the value observed for PTU (FIG. 13). Next, a secondary screen was executed using 50 μM of each compound for the four compounds that provided 100% inhibition in the primary screen (FIG. 13). Two compounds, ZINC05626394 and ZINC39395747 exhibited 100% inhibition. These two potent inhibitors were tested at lower concentrations to determine the $IC_{50}$ values shown in FIG. 13. It should be noted that ZINC05626394 and ZINC39395747 have $IC_{50}$ values of 10.84 μM and 18.41 μM respectively, a major improvement over PTU's $IC_{50}$ value of 279.4 μM.

Structure-Activity Relationship Screen

Figure 14:
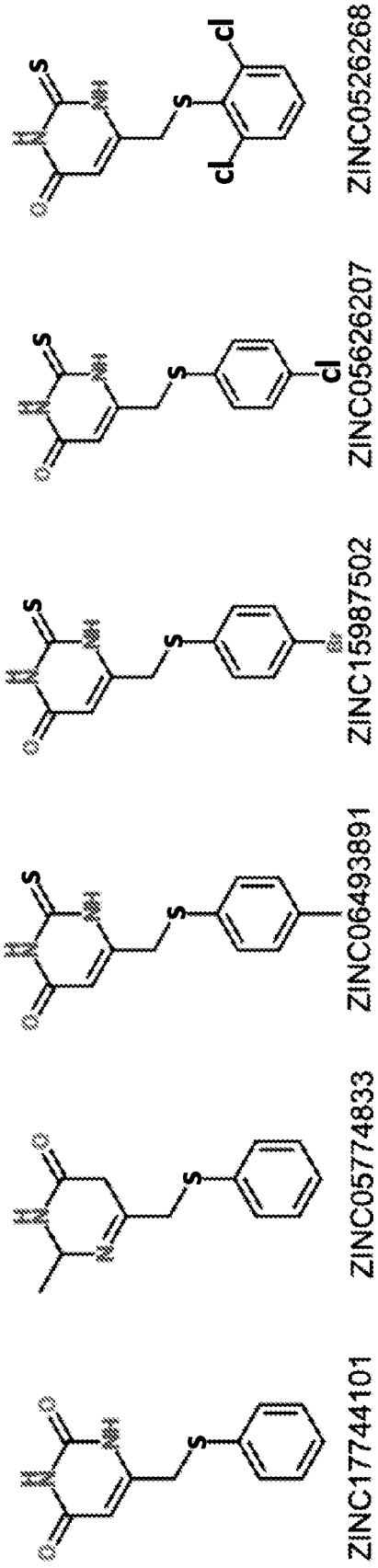
FIG. 14. List of ZINC compounds with modified benzene rings of ZINC05626394. Structures show ZINC05626394 as the parent structure with modified benzene rings.
Figure 15:
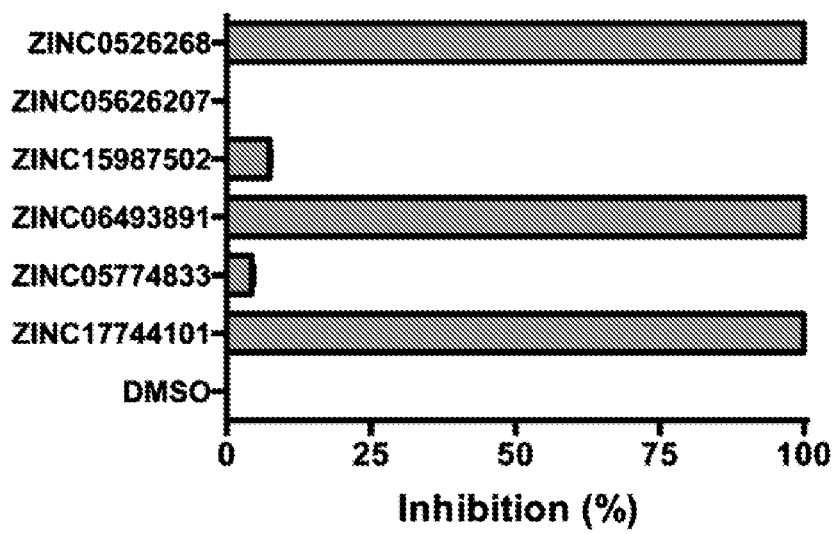
FIG. 15. Modification of the ZIN05626394 benzene rings and analysis of the importance of prosthetic benzene rings. Six compounds were screened based on the structure of ZINC05626394 and tested for inhibitory effect on CyB5R3 at 500 μM concentrations; of these 3 compounds with 100% inhibition effect were used for secondary screening at 50 μM concentration and ZINC0526268 was identified. The calculated $IC_{50}$ value of this compound is 15.06 μM.
Figure 15:
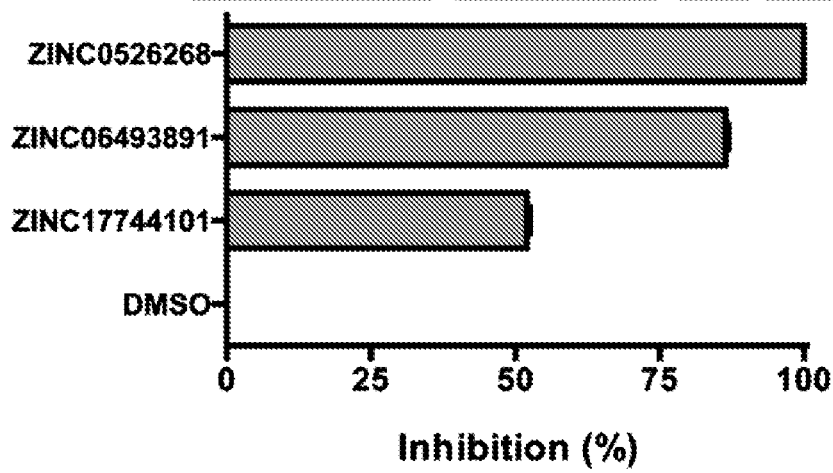
Figure 15:
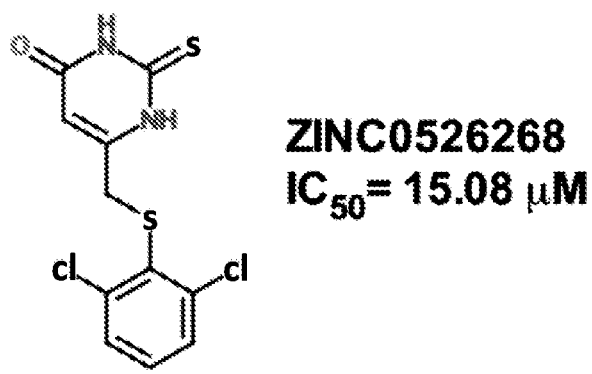

Compounds were identified that are chemically similar to ZINC05626394 using the 70% similarity search of the ZINC database of commercially available compounds. Two series of compounds were selected that established a SAR around the pyrimidine and phenyl ring of ZINC05626394. The first series consists of two compounds that substitute the sulfur on the pyrimidine ring for an oxygen (ZINC05774833) or a carbon (ZINC17744101) (FIG. 14). Interestingly, the replacement of sulfur by oxygen in ZINC17744101 showed 100% inhibition using 500 μM and 50% inhibition at 50 μM whereas PTU showed little inhibition at the 50 μM concentration (FIG. 15). As expected, the S—CH3 modification (ZINC05774833) abolished all inhibitory effects even at the 500 uM concentration (FIG. 15).

Figure 16:
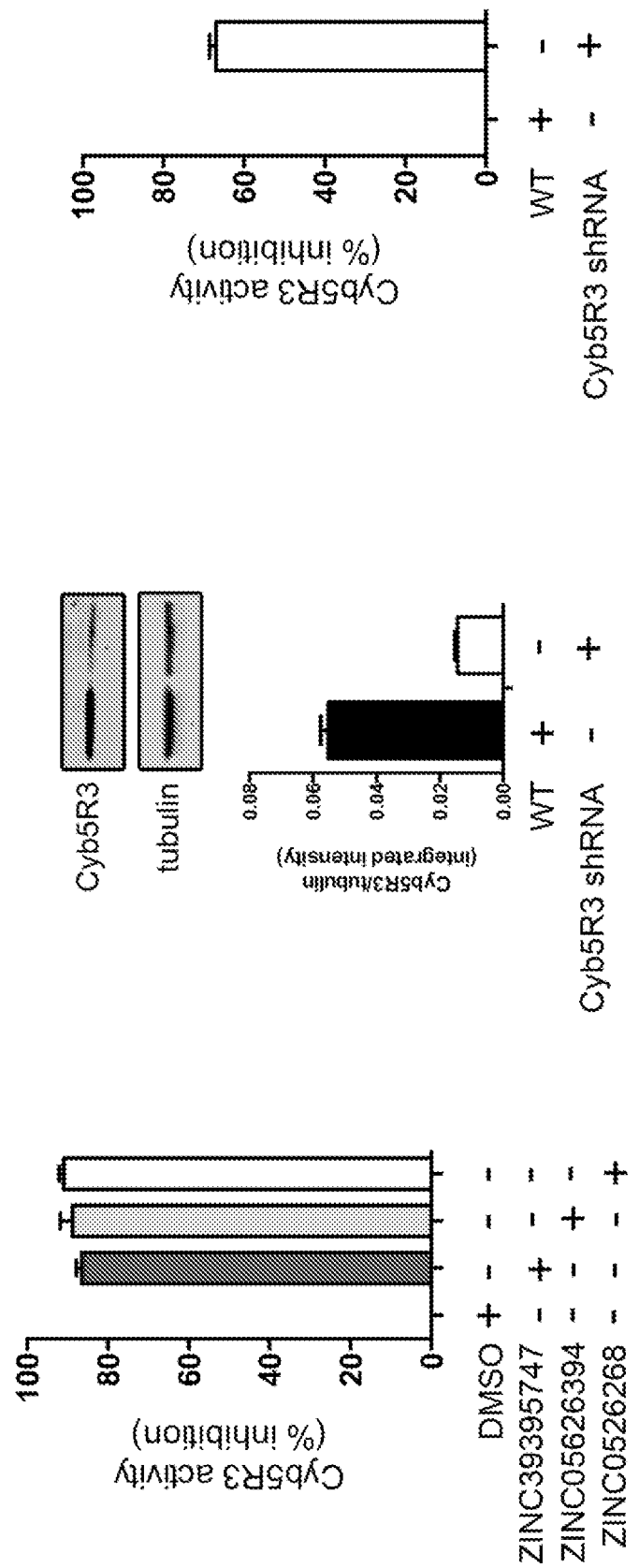
FIG. 16. Cyb5R3 activity measurements in HEK cells with Cyb5R3 inhibitors. a, HEKs cells were incubated with 21.86 μM of ZINC05626394, 36.82 μM of ZINC39395747 and 30.16 μM of ZINC0526268 for 24 hours and subjected to a Cyb5R3 activity assay. HEK knockdown cells for Cyb5R3 served as a control positive control for the assay.

To determine if the most potent compounds, ZINC05626394, ZINC39395747 and ZINC0526268, exert inhibitory activity HEK cells were subjected to a Cyb5R3 activity assay. The results confirm that each inhibitor causes >80% inhibition of cellular Cyb5R3 activity (FIG. 16). Specificity of the assay was also tested using stable HEK Cyb5R3 knockdown cells using lentivirus. Knockdown of Cyb5R3 protein was approximately 95%, which resulted in 95% loss in activity (FIG. 16). These results confirm that each compound has inhibitory action on Cyb5R3 activity in a biological setting.

Figure 17:
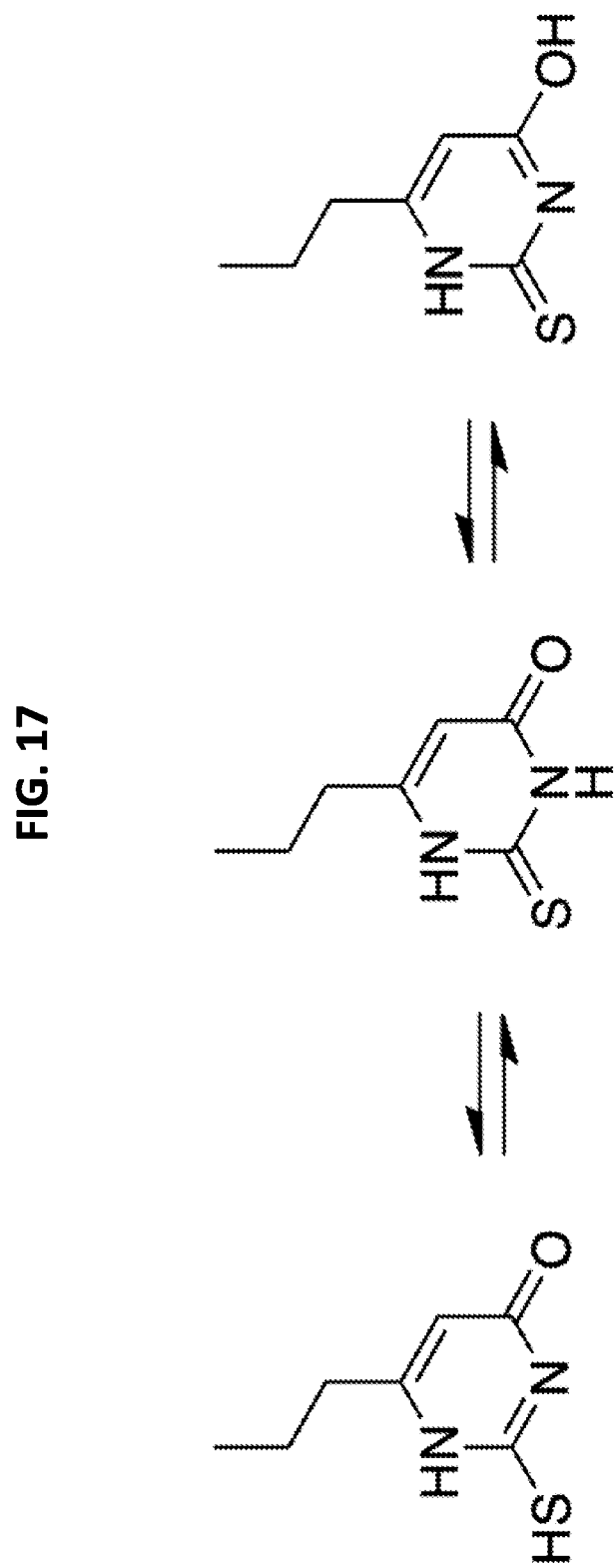
FIG. 17. Potential mechanism of propylthiouracil tautomerization into different isomers. The predominant middle isomer can tautomerize towards a thiol type form (left) and towards an enol type form (right).

The activity of PTU to treat hyperthyroidism may depend on its ability to function as a thiol, which could also be the case for the inhibition of Cyb5R3 activity. And, given the similarity of the compounds to PTU, one cannot rule out the possibility that a similar effect could be taking place in the SARs. More specifically PTU exists in three tautomeric forms where the thione form predominates (FIG. 17). The principal thione/lactam form shown in FIG. 8 can likely tautomerize towards a thiol type tautomer and an enol type tautomer. These different tautomers have various interaction possibilities with Cyb5R3. The thiol tautomer creates the possibility to form a disulfide bridge with Cys273, which lies next to the predicted binding site of PTU. Consequently, it is possible that the inhibitors all should have a double bonded sulfur since inhibition is achieved via this covalent bond between Cys273 and the inhibitor. Although the sulfur is important for the potency of the compounds it does not seem essential as demonstrated with ZINC17744101, as this compound has the sulfur replaced by a double bonded oxygen. In addition, the three tautomers have different hydrogen-bond formation possibilities with Cyb5R3 and a closer look at the key interacting residues suggests they all can either act as donors or acceptors. This reciprocity between donor/acceptor roles and tautomers may contribute to the potency of these compounds.

An explanation for the less potent ketone compound ZINC05774833 could be due to the favorable properties of the thione in the binding site. This sub pocket is where the thione is placed as an apolar character and as a result the double bonded sulfur is less polar than the double bonded oxygen because it is less electronegative. The ketone compound doesn't lie as comfortable in the pocket as the thione form, which is displayed by their respective $IC_{50}$ values.

Sulfur has a wide range of oxidation states from −2 to +6 because of its ability to use d-orbitals to accept electrons. These are all present in biological reactions and this could intervene with electron transfer processes described here, the reduction of potassium ferricyanide only with PTU shows no reduction, which suggests that PTU has no intrinsic reductive properties. In fact, all the compounds screened showed no intrinsic reduction (data not shown).

For the second compound series various decorations of the phenyl ring were explored. Chlorine substituents in the ortho position (ZINC05626207) eliminated activity. Carbon (ZINC06493891), chlorine (ZINC05626207), and bromine (ZINC15987502) in the para position define an SAR where activity increases with atomic mass. Although none of these compounds have higher activity than the undecorated phenyl, these results, along with the micro-molar ZINC39395747 inhibitor where the phenyl is substituted with a benzoxazole, suggest this ring is a good starting point for further development.

In view of the many possible embodiments to which the principles of the disclosed invention may be applied, it should be recognized that the illustrated embodiments are only preferred examples of the invention and should not be taken as limiting the scope of the invention.

What is claimed is:

1. A method for treating massive hemoptysis, GI bleed, epistaxis, migraine headache (post-prodome), musculoskeletal injuries in the acute phase, bleeding diatheses, anaphylactic shock, agioedema, urticaria in a subject, comprising administering to a subject in need thereof, a therapeutically effective amount of a compound, or a pharmaceutically acceptable salt thereof, having a structure of:

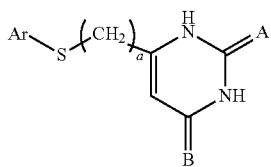

wherein A and B are each individually selected from O or S;
a is 1 to 4; and
Ar is optionally substituted aryl or optionally substituted heteroaryl.

2. The method of claim 1, wherein A is O and B is O.
3. The method of claim 1, wherein a is 1.
4. The method of claim 1, wherein Ar is phenyl or substituted phenyl having a structure of:

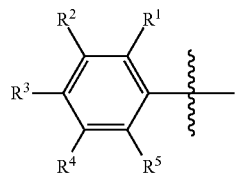

wherein $R^1$ to $R^5$ are each individually selected from H, optionally substituted alkyl (particularly lower alkyl), or halogen.

5. The method of claim 4, wherein $R^3$ is optionally substituted alkyl or halogen; and $R^1$, $R^2$, $R^4$ and $R^5$ are each H.

6. The method of claim 4, wherein $R^1$ and $R^5$ are each individually selected from halogen, and $R^2$ to $R^4$ are each H.
7. The method of claim 1, wherein Ar is optionally substituted benzoxazole.
8. The method of claim 7, wherein Ar is:

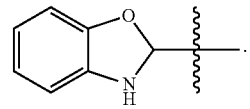 [SMILES: *C1Nc2ccccc2O1]

9. The method of claim 1, wherein A is S and B is O.
10. The method of claim 9, wherein the compound is a tautomer.
11. The method of claim 1, further comprising co-administering to the subject a therapeutically effective amount of a nitrite, a nitrate, a nitrodilator, an inhibitor of sGC, or a stimulator of sGC.
12. The method of claim 1, wherein the method comprises treating anaphylactic shock.
13. The method of claim 12, wherein A is S and B is O.
14. The method of claim 13, wherein the compound is a tautomer.
15. The method of claim 12, comprising chronic administration of the compound, or a pharmaceutically acceptable salt thereof, to the subject.
16. The method of claim 1, comprising chronic administration of the compound, or a pharmaceutically acceptable salt thereof, to the subject.
17. The method of claim 1, comprising initially administering the compound, or a pharmaceutically acceptable salt thereof, to the subject and subsequently administering the compound, or a pharmaceutically acceptable salt thereof, to the subject, wherein the subsequent administration occurs at least 24 hours after the initial administration.
18. The method of claim 1, comprising initially administering the compound, or a pharmaceutically acceptable salt thereof, to the subject and subsequently administering the compound, or a pharmaceutically acceptable salt thereof, to the subject, wherein the subsequent administration occurs more than 24 hours after the initial administration.
19. The method of claim 1, comprising administering the compound, or a pharmaceutically acceptable salt thereof, to the subject on consecutive days.
20. A method for treating massive hemoptysis, GI bleed, epistaxis, migraine headache (post-prodome), musculoskeletal injuries in the acute phase, trauma, hemangioma repair and other intraoperative causes of excessive bleeding, bleeding diatheses, uterine hemorrhage or menorrhagia, septic shock, anaphylactic shock, agioedema, urticaria, or allergic rhinosinusitis in a subject, comprising administering to a subject in need thereof, a therapeutically effective amount of a compound, or a pharmaceutically acceptable salt thereof, having a structure of:

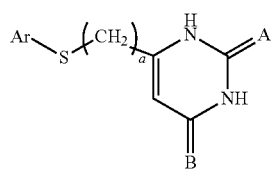

wherein A and B are each individually selected from O or S;

a is 1 to 4; and
Ar has a structure of:

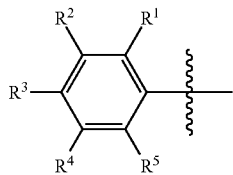

wherein $R^1$ to $R^5$ are each individually selected from H, optionally substituted alkyl (particularly lower alkyl), or halogen; or Ar is optionally substituted benzoxazole.

21. The method of claim 20, wherein A is S; B is O; a is 1; and Ar is:

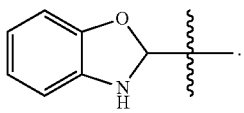

22. The method of claim 20, wherein the method comprises treating anaphylactic shock.

23. The method of claim 22, wherein A is S and B is O.

24. The method of claim 23, wherein the compound is a tautomer.

25. The method of claim 22, wherein A is S; B is O; a is 1; and Ar is:

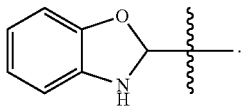 [SMILES: *C1Nc2ccccc2O1]

26. The method of claim 21, comprising chronic administration of the compound, or a pharmaceutically acceptable salt thereof, to the subject.

27. The method of claim 20, comprising initially administering the compound, or a pharmaceutically acceptable salt thereof, to the subject and subsequently administering the compound, or a pharmaceutically acceptable salt thereof, to the subject, wherein the subsequent administration occurs at least 24 hours after the initial administration.

28. The method of claim 20, comprising initially administering the compound, or a pharmaceutically acceptable salt thereof, to the subject and subsequently administering the compound, or a pharmaceutically acceptable salt thereof, to the subject, wherein the subsequent administration occurs more than 24 hours after the initial administration.

29. The method of claim 20, comprising administering the compound, or a pharmaceutically acceptable salt thereof, to the subject on consecutive days.

30. A method for treating massive hemoptysis, GI bleed, epistaxis, migraine headache (post-prodome), musculoskeletal injuries in the acute phase, trauma, hemangioma repair and other intraoperative causes of excessive bleeding, bleeding diatheses, uterine hemorrhage or menorrhagia, septic shock, anaphylactic shock, agioedema, urticaria, or allergic rhinosinusitis in a subject, comprising co-administering to a subject in need thereof, a therapeutically effective amount of a compound, or a pharmaceutically acceptable salt thereof, having a structure of:

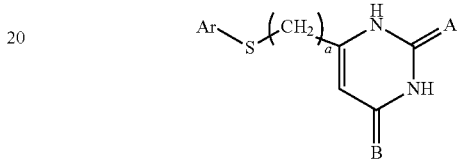

wherein A and B are each individually selected from O or S;

a is 1 to 4; and

Ar is optionally substituted aryl or optionally substituted heteroaryl; and a therapeutically effective amount of a nitrite, a nitrate, a nitrodilator, an inhibitor of sGC, or a stimulator of sGC.

31. The method of claim 30, comprising chronic administration of the compound, or a pharmaceutically acceptable salt thereof, to the subject.

32. The method of claim 30, comprising initially administering the compound, or a pharmaceutically acceptable salt thereof, to the subject and subsequently administering the compound, or a pharmaceutically acceptable salt thereof, to the subject, wherein the subsequent administration occurs at least 24 hours after the initial administration.

33. The method of claim 30, comprising initially administering the compound, or a pharmaceutically acceptable salt thereof, to the subject and subsequently administering the compound, or a pharmaceutically acceptable salt thereof, to the subject, wherein the subsequent administration occurs more than 24 hours after the initial administration.

34. The method of claim 30, comprising administering the compound, or a pharmaceutically acceptable salt thereof, to the subject on consecutive days.

* * * * *